(12) United States Patent
Kopelman et al.

(10) Patent No.: US 11,367,192 B2
(45) Date of Patent: Jun. 21, 2022

(54) FOREIGN OBJECT FILTERING FOR INTRAORAL SCANNING

(71) Applicant: Align Technology, Inc., San Jose, CA (US)

(72) Inventors: Avi Kopelman, Palo Alto, CA (US); Michael Sabina, Campbell, CA (US)

(73) Assignee: Align Technology, Inc., San Jose, CA (US)

( * ) Notice: Subject to any disclaimer, the term of this patent is extended or adjusted under 35 U.S.C. 154(b) by 84 days.

(21) Appl. No.: 16/809,451

(22) Filed: Mar. 4, 2020

(65) Prior Publication Data

US 2020/0281700 A1 Sep. 10, 2020

Related U.S. Application Data

(60) Provisional application No. 62/815,954, filed on Mar. 8, 2019.

(51) Int. Cl.
*G06K 9/00* (2022.01)
*G06T 7/00* (2017.01)
(Continued)

(52) U.S. Cl.
CPC .............. *G06T 7/0014* (2013.01); *A61B 1/24* (2013.01); *A61C 7/002* (2013.01); *A61C 9/0053* (2013.01);
(Continued)

(58) Field of Classification Search
CPC ...... A22C 17/0006; A22C 17/02; A47J 43/18; A61B 1/00009; A61B 1/00108; A61B 1/24; A61C 13/0004; A61C 7/002; A61C 9/0046; A61C 9/0053; A61C 9/006; A61C 9/0073; F16M 11/105; F16M 11/14; F24S 2050/25; F24S 23/77; G06N 20/00; G06N 3/0445; G06N 3/0454; G06N 3/084; G06T 17/00; G06T 19/20; G06T 2200/08;
(Continued)

(56) References Cited

U.S. PATENT DOCUMENTS 7,698,068 B2 4/2010 Babayoff
8,932,058 B2 1/2015 Fisker et al.
(Continued)

FOREIGN PATENT DOCUMENTS

WO 2018005009 A1 1/2018

OTHER PUBLICATIONS

International Search Report and Written Opinion of the International Application No. PCT/US2020/021264 dated Jun. 15, 2020, 15 pages.

*Primary Examiner* — Xin Jia
(74) *Attorney, Agent, or Firm* — Lowenstein Sandler LLP

(57) ABSTRACT

In a method of generating a virtual 3D model of a dental site, scan data comprising an intraoral image is received during an intraoral scan of a dental site. A representation of a foreign object is identified in the intraoral image based on an analysis of the scan data. The intraoral image is modified by removing the representation of the foreign object from the intraoral image. Additional scan data comprising a plurality of additional intraoral images of the dental site is received during the intraoral scan. A virtual 3D model of the dental site is then generated using the modified intraoral image and the plurality of additional intraoral images.

23 Claims, 14 Drawing Sheets

(51) Int. Cl.
*A61C 9/00* (2006.01)
*A61C 7/00* (2006.01)
*G06T 17/00* (2006.01)
*G06T 19/20* (2011.01)
*G06T 7/70* (2017.01)
*G16H 30/40* (2018.01)
*G16H 50/50* (2018.01)
*G06N 20/00* (2019.01)
*A61B 1/24* (2006.01)
*A61B 1/00* (2006.01)

(52) U.S. Cl.
CPC ............ *A61C 9/0073* (2013.01); *G06N 20/00* (2019.01); *G06T 7/70* (2017.01); *G06T 17/00* (2013.01); *G06T 19/20* (2013.01); *G16H 30/40* (2018.01); *G16H 50/50* (2018.01); *A61B 1/00009* (2013.01); *A61B 1/00108* (2013.01); *G06T 2200/08* (2013.01); *G06T 2207/30036* (2013.01); *G06T 2210/41* (2013.01)

(58) Field of Classification Search
CPC . G06T 2207/10016; G06T 2207/20081; G06T 2207/20084; G06T 2207/30036; G06T 2210/41; G06T 7/0014; G06T 7/11; G06T 7/55; G06T 7/70; G16H 30/40; G16H 50/20; G16H 50/50; Y02E 10/40
See application file for complete search history.

(56) References Cited

U.S. PATENT DOCUMENTS

| | | |
|---|---|---|
| 10,111,714 B2 | 10/2018 | Kopelman et al. |
| 2009/0129639 A1* | 5/2009 | Ortega ................. A61B 6/5223 382/128 |
| 2014/0067334 A1 | 3/2014 | Kuo |
| 2015/0164335 A1 | 6/2015 | Van Der Poel et al. |
| 2016/0256035 A1* | 9/2016 | Kopelman ........... A61C 9/0053 |
| 2020/0170760 A1* | 6/2020 | Dawood ............... G06K 9/4652 |

* cited by examiner

1550

```
┌─────────────────────────────────────────────────────────────────┐
│ Apply a first orthodontic appliance to a patient's teeth to     │
│ reposition the teeth from a first tooth arrangement to a        │
│ second tooth arrangement 1560                                   │
└─────────────────────────────────────────────────────────────────┘
                              │
                              ▼
┌─────────────────────────────────────────────────────────────────┐
│ Apply a second orthodontic appliance to the patient's teeth to  │
│ reposition the teeth from the second tooth arrangement to a     │
│ third tooth arrangement 1570                                    │
└─────────────────────────────────────────────────────────────────┘
```

```
┌─────────────────────────────────────────────────────────────────┐
│ Determine a movement path to move one or more teeth from an     │
│ initial arrangement to a target arrangement                     │
│ 1610                                                            │
└─────────────────────────────────────────────────────────────────┘
                              │
                              ▼
┌─────────────────────────────────────────────────────────────────┐
│ Determine a force system to produce movement of the one or      │
│ more teeth along the movement path                              │
│ 1620                                                            │
└─────────────────────────────────────────────────────────────────┘
                              │
                              ▼
┌─────────────────────────────────────────────────────────────────┐
│ Determine an arch or palate expander design for an orthodontic  │
│ appliance configured to produce the force system                │
│ 1630                                                            │
└─────────────────────────────────────────────────────────────────┘
                              │
                              ▼
┌─────────────────────────────────────────────────────────────────┐
│ Determine instructions for fabrication of the orthodontic       │
│ appliance (or mold that will be used to manufacture orthodontic │
│ appliance), optionally incorporating the arch or palate         │
│ expander design 1640                                            │
└─────────────────────────────────────────────────────────────────┘
```

FIG. 16

FOREIGN OBJECT FILTERING FOR INTRAORAL SCANNING

RELATED APPLICATIONS

This patent application claims the benefit under 35 U.S.C. § 119(e) of U.S. Provisional Application No. 62/815,954, filed Mar. 8, 2019, which is herein incorporated by reference.

TECHNICAL FIELD

Embodiments of the present disclosure relate to the field of intraoral scanning and, in particular, to a system and method for performing real-time filtering of intraoral images generated during intraoral scanning.

BACKGROUND

In prosthodontic procedures designed to insert a dental prosthesis in the oral cavity, the dental site at which the prosthesis is to be implanted in many cases should be measured accurately and studied carefully, so that a prosthesis such as a crown, denture or bridge, for example, can be properly designed and dimensioned to fit in place. A good fit enables mechanical stresses to be properly transmitted between the prosthesis and the jaw, and to prevent infection of the gums via the interface between the prosthesis and the dental site, for example.

Some procedures also call for removable prosthetics to be fabricated to replace one or more missing teeth, such as a partial or full denture, in which case the surface contours of the areas where the teeth are missing need to be reproduced accurately so that the resulting prosthetic fits over the edentulous region with even pressure on the soft tissues.

In some practices, the dental site is prepared by a dental practitioner, and a positive physical model of the dental site is constructed using known methods. Alternatively, the dental site may be scanned to provide 3D data of the dental site (i.e. in the form of intraoral images such as height maps). In either case, the virtual or real model of the dental site is sent to the dental lab, which manufactures the prosthesis based on the model. However, if the model is deficient or undefined in certain areas, or if the preparation was not optimally configured for receiving the prosthesis, the design of the prosthesis may be less than optimal. For example, if the insertion path implied by the preparation for a closely-fitting coping would result in the prosthesis colliding with adjacent teeth, the coping geometry has to be altered to avoid the collision, which may result in the coping design being less optimal. Further, if the area of the preparation containing a finish line lacks definition, it may not be possible to properly determine the finish line and thus the lower edge of the coping may not be properly designed. Indeed, in some circumstances, the model is rejected and the dental practitioner then re-scans the dental site, or reworks the preparation, so that a suitable prosthesis may be produced.

In orthodontic procedures it can be important to provide a model of one or both jaws. Where such orthodontic procedures are designed virtually, a virtual model of the oral cavity is also beneficial. Such a virtual model may be obtained by scanning the oral cavity directly, or by producing a physical model of the dentition, and then scanning the model with a suitable scanner.

Thus, in both prosthodontic and orthodontic procedures, obtaining a three-dimensional (3D) model of a dental site in the oral cavity is an initial procedure that is performed. When the 3D model is a virtual model, the more complete and accurate the scans of the dental site are, the higher the quality of the virtual model, and thus the greater the ability to design an optimal prosthesis or orthodontic treatment appliance(s).

During an intraoral scanning session, often there are foreign objects that are disposed within a patient's mouth. Such foreign objects may reduce an accuracy of the generated virtual model. For example, image processing algorithms may adjust the shape of one or more regions of a dental arch based on the shape of the foreign object under the assumption that the foreign object is a part of the dental arch. Additionally, foreign objects may move between the generation of different intraoral images, which may interfere with image registration.

SUMMARY

In a first aspect of the disclosure, a method comprises receiving scan data comprising an intraoral image during an intraoral scan of a dental site, identifying a representation of a foreign object in the intraoral image based on an analysis of the scan data, modifying the intraoral image by removing the representation of the foreign object from the intraoral image, receiving additional scan data comprising a plurality of additional intraoral images of the dental site during the intraoral scan, and generating a virtual three-dimensional (3D) model of the dental site using the modified intraoral image and the plurality of additional intraoral images.

A second aspect of the disclosure may extend the first aspect of the disclosure. In the second aspect of the disclosure, the method further includes identifying an additional representation of the foreign object in one of more additional intraoral images of the plurality of additional intraoral images of the dental site, and modifying the one or more additional intraoral images by removing the additional representation of the foreign object from the one or more additional intraoral images, wherein the foreign object is a stationary object that has a same position at the dental site in the intraoral image and the one or more additional intraoral images.

A third aspect of the disclosure may extend the first or second aspect of the disclosure. In the third aspect of the disclosure, the method further includes analyzing the scan data to determine at least one of a reflectivity of the foreign object, a diffraction of the foreign object, a reactivity of the foreign object to a wavelength of light, a texture of the foreign object, a surface pattern of the foreign object, a color of the foreign object or a shape of the foreign object; and identifying the representation of the foreign object based on at least one of the reflectivity of the foreign object, the diffraction of the foreign object, the reactivity of the foreign object to a wavelength of light, the texture of the foreign object, the surface pattern of the foreign object, the color of the foreign object or the shape of the foreign object.

A fourth aspect of the disclosure may extend the first through third aspects of the disclosure. In the fourth aspect of the disclosure, the method further includes performing image processing on the intraoral image to determine a plurality of shapes in the intraoral image, the plurality of shapes comprising the shape of the foreign object, comparing the plurality of shapes in the intraoral image to a plurality of known shapes of reference objects, and determining that the shape of the foreign object matches a known shape of a reference object as a result of the comparing.

A fifth aspect of the disclosure may extend the fourth aspect of the disclosure. In the fifth aspect of the disclosure, the method further includes performing the following before the intraoral scan of the dental site: entering a training mode, receiving a plurality of images of the foreign object during the training mode, generating a virtual model of the foreign object based on the plurality of images, and adding at least one of the virtual model of the foreign object or the plurality of images of the foreign object to a reference object library that comprises the plurality of known shapes of the reference objects.

A sixth aspect of the disclosure may extend the first through fifth aspect of the disclosures. In the sixth aspect of the disclosure, the method further includes performing image processing of the intraoral image to identify at least one of a plurality of textures or a plurality of surface patterns in the intraoral image, determining at least one of a texture of the plurality of textures or a surface pattern of the plurality of surface patterns that is not naturally occurring at the dental site, and determining a contour of a region of the intraoral image having at least one of the texture or the surface pattern that is not naturally occurring at the dental site, wherein the region of the intraoral image within the contour is removed from the intraoral image.

A seventh aspect of the disclosure may extend the sixth aspect of the disclosure. In the seventh aspect of the disclosure, determining at least one of the texture or the surface pattern that is not naturally occurring at the dental site comprises at least one of: a) comparing the plurality of textures identified in the intraoral image to a plurality of known textures of reference objects, and determining that the at least one texture matches a known texture of a reference object as a result of the comparing; b) comparing the plurality of surface patterns identified in the intraoral image to a plurality of known surface patterns of reference objects, and determining that the at least one surface patterns matches a known surface pattern of a reference object as a result of the comparing; c) comparing the plurality of textures identified in the intraoral image to a plurality of known textures that naturally occur at the dental site, and determining that the at least one texture fails to match any known texture that naturally occurs in the mouth as a result of the comparing; or d) comparing the plurality of surface patterns identified in the intraoral image to a plurality of known surface patterns that naturally occur at the dental site, and determining that the at least one surface pattern fails to match any known surface pattern that naturally occurs in the mouth as a result of the comparing.

An eighth aspect of the disclosure may extend the first through seventh aspects of the disclosure. In the eighth aspect of the disclosure, the method further includes performing image processing of the intraoral image to identify a plurality of colors in the intraoral image, determining at least one color of the plurality of colors that is not naturally occurring at the dental site, and determining a contour of a region of the intraoral image having the at least one color that is not naturally occurring at the dental site, wherein the region of the intraoral image within the contour is removed from the intraoral image.

A ninth aspect of the disclosure may extend the eighth aspect of the disclosure. In the ninth aspect of the disclosure, the method further includes determining the at least one color that is not naturally occurring at the dental site comprises performing the following for each pixel or voxel of the intraoral image, determining, for each color channel of a color encoding system, at least one of a saturation value or an intensity value, determining a tuple comprising at least one of the saturation value or the intensity value for each color channel of the color encoding system, determining that the tuple is outside of a specified color range, and determining a contour of the region in the intraoral image having the at least one color that is not naturally occurring comprises determining a plurality of contiguous pixels or voxels having tuples that are outside of the specified color range.

A tenth aspect of the disclosure may extend the first through ninth aspects of the disclosure. In the tenth aspect of the disclosure, the method further includes receiving an indication that the foreign object is at the dental site, the indication comprising an identification of the foreign object, querying a reference object library using the identification of the foreign object; receiving a response to the query, the response comprising one or more known properties of the foreign object, the one or more known properties comprising at least one of a known reflectivity of the foreign object, a known diffraction of the foreign object, a known reactivity of the foreign object to the wavelength of light, a known texture of the foreign object, a known surface pattern of the foreign object, a known color of the foreign object or a known shape of the foreign object; and using the one or more known properties of the foreign object to identify the representation of the foreign object in the intraoral image.

An eleventh aspect of the disclosure may extend the first through tenth aspects of the disclosure. In the eleventh aspect of the disclosure, the method further includes, during the intraoral scan, generating a view of the intraoral site based on the modified intraoral image and the one or more additional intraoral images; generating an outline of the foreign object; adding the outline of the foreign object to the view; and providing a user interface that enables a user to select the outline of the foreign object, wherein user selection of the outline of the foreign object causes the representation of the foreign object to be added back to the intraoral image and further causes the foreign object to be added to a reference object library of known objects not to be filtered out.

A twelfth aspect of the disclosure may extend the first through eleventh aspects of the disclosure. In the twelfth aspect of the disclosure, the method further includes performing the following prior to modifying the intraoral image: determining a confidence value associated with the representation of the foreign object; determining that the confidence value is below a confidence threshold; presenting an option to a) remove the representation of the foreign object from the intraoral image or b) leave the representation of the foreign object in the intraoral image; and receiving a user selection to remove the representation of the foreign object from the intraoral image.

A thirteenth aspect of the disclosure may extend the twelfth aspect of the disclosure. In the thirteenth aspect of the disclosure, the method further includes determining one or more properties of the foreign object, the one or more properties comprising at least one of a reflectivity of the foreign object, a diffraction of the foreign object, a reactivity of the foreign object to the wavelength of light, a texture of the foreign object, a surface pattern of the foreign object, a color of the foreign object or a shape of the foreign object; and adding an entry for the foreign object to a reference object library of known foreign objects to be filtered out.

A fourteenth aspect of the disclosure may extend the twelfth or thirteenth aspect of the disclosure. In the fourteenth aspect of the disclosure, identifying the representation of the foreign object comprises: processing the intraoral image using a machine learning model that has been trained to identify foreign objects at dental sites; and receiving an output of the machine learning model, wherein the output comprises a binary mask that has a number of entries that is equal to a number of pixels or voxels in the intraoral image, wherein entries associated with pixels or voxels that are part of the foreign object have a first value and wherein entries associated with pixels or voxels that are not part of the foreign object have a second value; wherein the intraoral image is modified using the binary mask.

In a fifteenth aspect of the disclosure, a method comprises receiving intraoral scan data comprising a plurality of images of a dental site; generating a virtual three-dimensional (3D) model of the dental site based on the plurality of images; performing an analysis on an image of the dental site; identifying a representation of a reference object in the image, wherein the reference object has one or more known properties; and modifying at least one of the image or the virtual 3D model of the dental site by adding additional data about the reference object to at least one of the image or the virtual 3D model based on the one or more known properties of the reference object.

A sixteenth aspect of the disclosure may extend the fifteenth aspect of the disclosure. In the sixteenth aspect of the disclosure, the image is one of the plurality of images of the dental site used to generate the virtual 3D model, the image is modified by adding the additional data about the reference object to the image, and the image, as modified, is used to generate the virtual 3D model of the dental site.

A seventeenth aspect of the disclosure may extend the sixteenth aspect of the disclosure. In the seventeenth aspect of the disclosure, the method further comprises performing image processing on the image to determine a probable object represented in the image, wherein the probable object comprises one or more physical properties; comparing the one or more physical properties of the probable object to the one or more known properties of the reference object; determining that the one or more physical properties of the probable object match the one or more known properties the reference object as a result of the comparing; and determining that the probable object is the reference object.

An eighteenth aspect of the disclosure may extend the seventeenth aspect of the disclosure. In the eighteenth aspect of the disclosure, the one or more physical properties comprise at least one of a reflectivity, a diffraction, a reactivity to a wavelength of light, a texture, a surface pattern, a color or a shape.

A nineteenth aspect of the disclosure may extend any of the fifteenth through the eighteenth aspect of the disclosure. In the nineteenth aspect of the disclosure, performing the analysis of the image comprises inputting the image into a machine learning model trained to identify one or more types of reference objects, wherein the machine learning model outputs an indication of the representation of the reference object in the image.

A twentieth aspect of the disclosure may extend the fifteenth or nineteenth aspect of the disclosure. In the twentieth aspect of the disclosure, the method further comprises generating the image on which the analysis is performed by projecting the virtual 3D model onto a plane.

A twenty first aspect of the disclosure may extend the twentieth aspect of the disclosure. In the twenty first aspect of the disclosure, the method further comprises: during an intraoral scan, generating a view of the dental site based on the modified image, wherein the view comprises an outline of the reference object based on the additional data about the reference object; receiving a plurality of additional images of the dental site during the intraoral scan; replacing one or more parts of a shape of the reference object based on the plurality of additional images; and updating the view of the dental site, the updated view showing those parts of the shape of the reference object that have been replaced.

A twenty second aspect of the disclosure may extend any of the fifteenth through the twenty first aspect of the disclosure. In the twenty second aspect of the disclosure, identifying the representation of the reference object comprises processing the image using a machine learning model that has been trained to identify one or more foreign objects at dental sites; and receiving an output of the machine learning model, wherein the output comprises a binary mask that has a number of entries that is equal to a number of pixels or voxels in the image, wherein entries associated with pixels or voxels that are part of the reference object have a first value and wherein entries associated with pixels or voxels that are not part of the reference object have a second value.

A twenty third aspect of the disclosure may extend any of the fifteenth through the twenty second aspect of the disclosure. In the twenty third aspect of the disclosure, the method further comprises performing the following before receiving the intraoral scan data: entering a training mode; receiving a plurality of images of the reference object during the training mode; generating a virtual model of the reference object based on the plurality of images of the reference object; and adding at least one of the virtual model of the reference object or the plurality of images of the reference object to a reference object library that comprises entries for a plurality of reference objects.

A twenty fourth aspect of the disclosure may extend any of the fifteenth through the twenty third aspect of the disclosure. In the twenty fourth aspect of the disclosure, the method further comprises receiving an indication that the reference object is at the dental site, the indication comprising an identification of the reference object; querying a reference object library comprising entries for a plurality of reference objects using the identification of the reference object; receiving a response to the query, the response comprising data associated with the reference object; and using the data to identify the reference object in the image.

A twenty fifth aspect of the disclosure may extend any of the fifteenth through the twenty fourth aspect of the disclosure. In the twenty fifth aspect of the disclosure, the one or more known properties comprise at least one of a known reflectivity of the reference object, a known diffraction of the reference object, a known reactivity of the reference object to a wavelength of light, a known texture of the reference object, a known surface pattern of the reference object, a known color of the reference object or a known shape of the reference object.

A twenty sixth aspect of the disclosure may extend any of the fifteenth through the twenty fifth aspect of the disclosure. In the twenty sixth aspect of the disclosure, the method further comprises determining a confidence value associated with the reference object; determining that the confidence value is below a confidence threshold; presenting an option to a) add the additional data about the reference object to at least one of the image or the virtual 3D model or b) leave a representation of the reference object in at least one of the image or the virtual 3D model unchanged; and receiving a user selection to add the additional data about the reference object to at least one of the image or the virtual 3D model.

A twenty seventh aspect of the disclosure may extend any of the fifteenth through the twenty sixth aspect of the disclosure. In the twenty seventh aspect of the disclosure, the reference object comprises at least one of a shape or a material that causes intraoral scans of the reference object to have a reduced accuracy.

A further aspect of the disclosure includes a computer readable medium comprising instructions that, when executed by a processing device, cause the processing device to perform the method of one or more of the first through twenty seventh aspects of the disclosure set forth above.

A further aspect of the disclosure includes a system comprising a handheld scanner to perform an intraoral scan, and a non-transitory computer readable medium comprising instructions that, when executed by a processor, cause the process to perform operations of the method of one or more of the first through twenty seventh aspects of the disclosure.

A further aspect of the disclosure includes a system comprising a handheld scanner to perform an intraoral scan, and a computing device that executes the method of one or more of the first through twenty seventh aspects of the disclosure.

BRIEF DESCRIPTION OF THE DRAWINGS

The present disclosure is illustrated by way of example, and not by way of limitation, in the figures of the accompanying drawings.

FIG. 15 illustrates a method of orthodontic treatment using a plurality of appliances, in accordance with embodiments.

FIG. 16 illustrates a method for designing an orthodontic appliance, in accordance with embodiments.

DETAILED DESCRIPTION

Figure 1A:
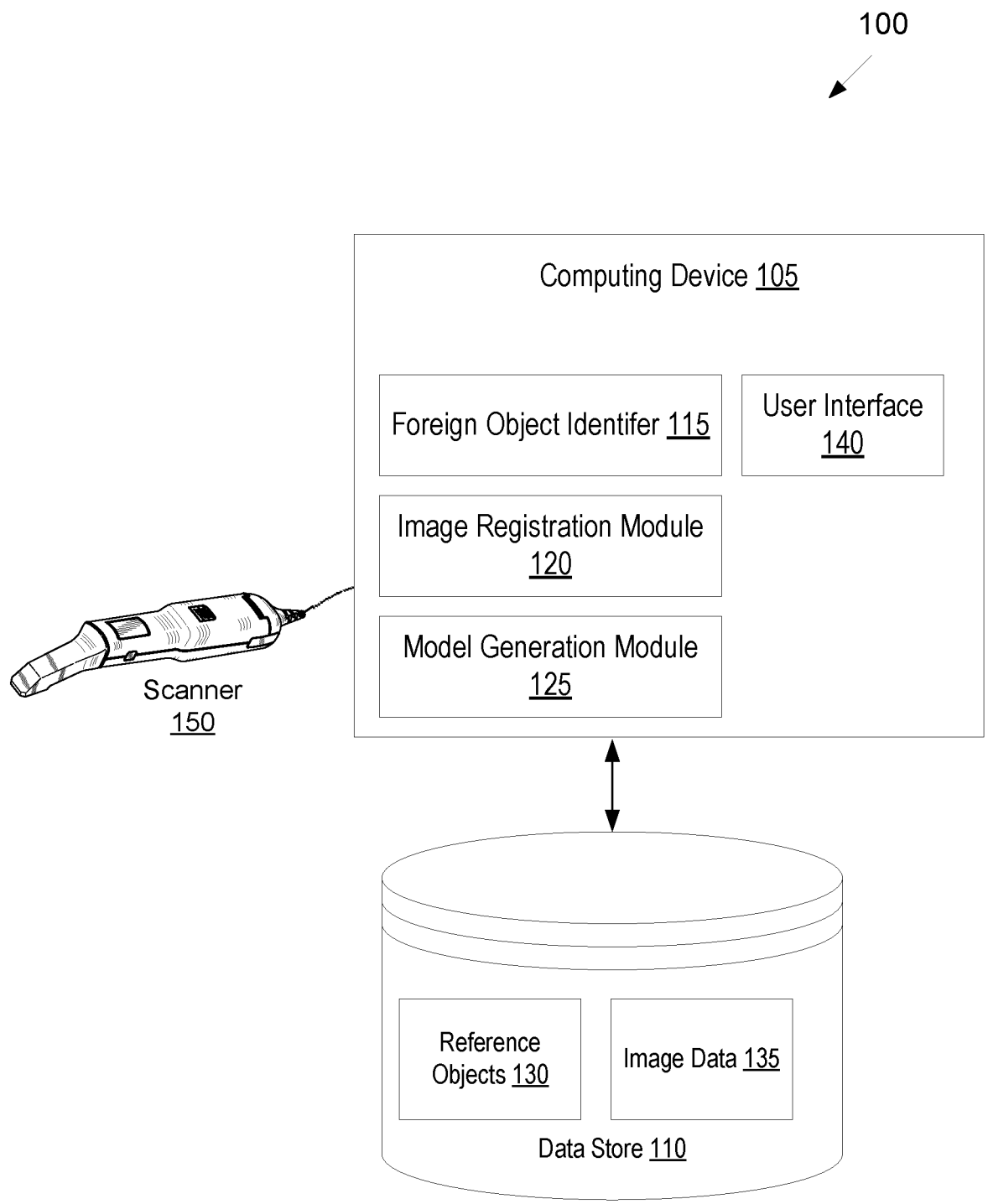
FIG. 1A illustrates one embodiment of a system for performing intraoral scanning and generating a virtual three dimensional model of a dental site.

Described herein is a method and apparatus for improving the quality of intraoral scans taken of dental sites that include one or more foreign objects. There are often interfering situations during intraoral scanning, where each interfering situation includes the presence of one or more foreign objects in intraoral images generated during an intraoral scan. The intraoral images may be or include height maps in some embodiments. For example, an intraoral image may be a 2D height map that includes a depth value for each pixel in the height map. An example of an intraoral scanner that generates such height maps during intraoral scanning is the iTero® intraoral digital scanner manufactured by Align Technology, Inc.

Foreign objects in intraoral scans (e.g., in intraoral images and/or height maps) may be objects that naturally occur in the mouth but that are not part of the dental arch being scanned (e.g., such as saliva, blood, tongue, bubbles, etc.). Such foreign objects may also be objects that do not naturally occur in the mouth (e.g., such as a cotton roll, a finger of an operator of an intraoral scanner, a suction device, an air blowing device, a dental mirror, a cord, a hand, a glove, and so on). The occurrence of foreign objects in the intraoral scan data (i.e. intraoral images) can slow down processing of those intraoral images and reduce the accuracy of a virtual 3D model generated from the intraoral images. Accordingly, embodiments described herein provide techniques for filtering out (i.e. removing) the depictions of foreign objects in real-time or near real-time (e.g., as the images are generated) before those foreign objects are used for image registration and/or virtual model generation. By removing the foreign objects from the intraoral images before performing further processing on those intraoral images, the speed and/or accuracy of the further processing may be increased. For example, the speed of image registration may be increased, the accuracy of image registration may be increased, the number of instances of failures to register images may be decreased, the accuracy of a generated 3D virtual model may be increased, and the speed of generating the 3D virtual model may be increased. Additionally, process intensive operations of accounting for and mitigating problems caused by foreign objects may be omitted, further increasing the speed of image processing.

Notably, the detection of foreign objects and removal of such foreign objects from intraoral images may be performed using a single image and may be performed on static (i.e. non-moving) objects. This is in contrast to many traditional techniques for identification and removal of unwanted moving objects from images (referred to as space carving techniques). Such traditional space carving techniques that identify and remove moving objects cannot work on a single image and do not work for objects that do not move between multiple frames of a video or multiple images of an area. In contrast, the techniques described herein may identify and remove stationary objects and may work on a single image.

In other embodiments, a known reference object may be identified in an image of a dental site (e.g., an intraoral image generated by an intraoral scanner or an image generated by projecting a virtual 3D model of a dental site onto a 3D surface or plane) and/or in a virtual 3D model of the dental site. The image and/or virtual 3D model of the dental site may then be modified by adding additional information about the reference object to the image and/or virtual 3D model based on known properties of the reference object.

In one embodiment, a computer-implemented method comprises receiving scan data comprising an intraoral image during an intraoral scan of a dental site and identifying a representation of a foreign object in the intraoral image based on an analysis of the scan data. The computer-implemented method further comprises modifying the intraoral image by removing the representation of the foreign object from the intraoral image. The computer-implemented method further comprises receiving additional scan data comprising a plurality of additional intraoral images of the dental site during the intraoral scan. The computer-implemented method further comprises generating a virtual three-dimensional (3D) model of the dental site using the modified intraoral image and the plurality of additional intraoral images.

In one embodiment, a non-transitory computer readable medium comprises instructions that, when executed by a processing device, cause the processing device to perform sequence of operations. The operations include receiving an intraoral image during an intraoral scan of a dental site and performing image processing on the intraoral image to determine a plurality of probable objects in the intraoral image, wherein each of the plurality of probable objects comprises one or more physical properties. The operations further include comparing, for each of the plurality of probable objects, the one or more physical properties of the probable object to a plurality of known properties of reference objects. The operations further include determining that one or more physical properties of a probable object of the plurality of probable objects match one or more known properties a reference object as a result of the comparing. The operations further include determining that the probable object is a foreign object at the intraoral site and then modifying the intraoral image by adding additional data about the foreign object to the intraoral image based on the one or more known properties of the reference object.

In one embodiment, a method of generating a virtual 3D model of a dental site includes receiving intraoral scan data comprising a plurality of images of a dental site. The method further includes generating a virtual three-dimensional (3D) model of the dental site based on the plurality of images. The method further includes performing an analysis on an image of the dental site. The image may be one of the images included in the received intraoral scan data. Alternatively, the image may be generated by projecting the virtual 3D model of the dental site onto a 2D surface or plane. The image may be or include a height map of the dental site. The method further includes identifying a representation of a reference object in the image, wherein the reference object has one or more known properties. The method further includes modifying at least one of the image or the virtual 3D model of the dental site by adding additional data about the reference object to at least one of the image or the virtual 3D model based on the one or more known properties of the reference object. The enables images and virtual 3D models to be improved by augmenting the image and/or virtual 3D model with accurate information about known reference objects. Thus, the accuracy of reference objects that are difficult to scan (e.g., those made of titanium) may be improved in images and virtual 3D models using techniques described herein.

In one embodiment, a system includes a handheld scanner to perform an intraoral scan and a non-transitory computer readable medium comprising instructions that, when executed by a processor, cause the process to perform the above described sequence of operations.

FIG. 1A illustrates one embodiment of a system 100 for performing intraoral scanning and/or generating a virtual three-dimensional (3D) model of a dental site. In one embodiment, system 100 carries out one or more operations of the below methods described with reference to FIGS. 1B-9. System 100 includes a computing device 105 that may be coupled to a scanner 150 and/or a data store 110.

Computing device 105 may include a processing device, memory, secondary storage, one or more input devices (e.g., such as a keyboard, mouse, tablet, and so on), one or more output devices (e.g., a display, a printer, etc.), and/or other hardware components. Computing device 105 may be connected to a data store 110 either directly or via a network. The network may be a local area network (LAN), a public wide area network (WAN) (e.g., the Internet), a private WAN (e.g., an intranet), or a combination thereof. The computing device 105 and/or the data store 110 may be integrated into the scanner 150 in some embodiments to improve performance and mobility.

Data store 110 may be an internal data store, or an external data store that is connected to computing device 105 directly or via a network. Examples of network data stores include a storage area network (SAN), a network attached storage (NAS), and a storage service provided by a cloud computing service provider. Data store 110 may include a file system, a database, or other data storage arrangement.

In some embodiments, a scanner 150 for obtaining three-dimensional (3D) data of a dental site in a patient's oral cavity (referred to as an intraoral scanner) is also operatively connected to the computing device 105. Scanner 150 may include a probe (e.g., a hand held probe) for optically capturing three dimensional structures (e.g., by confocal focusing of an array of light beams). One example of such a scanner 150 is the iTero® intraoral digital scanner manufactured by Align Technology, Inc. Other examples of intraoral scanners include the 3M™ True Definition Scanner and the Apollo DI intraoral scanner and CEREC AC intraoral scanner manufactured by Sirona®.

The scanner 150 may be used to perform an intraoral scan of a patient's oral cavity. A result of the intraoral scan may be a sequence of intraoral images that have been discretely generated (e.g., by pressing on a "generate image" button of the scanner for each image). Alternatively, a result of the intraoral scan may be one or more videos of the patient's oral cavity. An operator may start recording the video with the scanner 150 at a first position in the oral cavity, move the scanner 150 within the oral cavity to a second position while the video is being taken, and then stop recording the video. In some embodiments, recording may start automatically as the scanner identifies that it has been inserted into a patient oral cavity. The scanner 150 may transmit the discrete intraoral images (e.g., height maps) or intraoral video (referred to collectively as image data 135) to the computing device 105. Note that in some embodiments the computing device may be integrated into the scanner 150. Computing device 105 may store the image data 135 in data store 110. Alternatively, scanner 150 may be connected to another system that stores the image data in data store 110. In such an embodiment, scanner 150 may not be connected to computing device 105.

Computing device 105 may include a foreign object identifier 115, an image registration module 120, and/or a model generation module 125. The modules 115, 120, 125 may be software modules that are components of a single software application (e.g., different libraries of a single application), may be distinct software applications, may be firmware, may be hardware modules, and/or a combination thereof.

Foreign object identifier 115 may analyze received image data 135 (e.g., discrete intraoral images or intraoral images that are frames of an intraoral video) using one or more of the techniques described herein below to identify foreign objects in the intraoral images of the image data 135. In some embodiments, the data store 110 may include a reference object library that includes entries for one or more reference objects 130. The reference objects 130 may include well known equipment that is standard in dentist offices and/or orthodontist offices. Such reference objects 130 may be default reference objects that the data store 110 is prepopulated with. Some reference objects 130 may be custom reference objects that may have been generated by a dental practitioner using a training mode. Each entry for a reference object may include one or more physical properties of that reference object, such as a shape (e.g., a 3D virtual model of the reference object), color, texture, surface pattern, and so on. Some techniques for identifying foreign objects used by foreign object identifier 115 include determining physical properties of objects in a received intraoral image and comparing those physical properties of reference objects 130 in the reference object library. If a match is found, then an object represented in the intraoral image may be identified as a particular foreign object associated with the match.

In one embodiment a user may cause the foreign object identifier 115 to enter a training mode. During the training mode, the user may use the scanner 150 to perform a 3D scan of an object. Images of the 3D object may then be used to generate a virtual 3D model of the foreign object. An entry for the scanned foreign object may then be added to the reference objects 130. The entry may be for the same object and/or for other similar objects. The entry may include the generated virtual 3D model, a name of the object and/or one or more physical properties of the object.

If foreign object identifier 115 identifies a foreign object in an intraoral image, then foreign object identifier 115 may either filter out the foreign object from the intraoral image, leave the foreign object unchanged, or add further detailed information about the foreign object to the intraoral image (or otherwise augment the representation of the foreign object in the intraoral image).

Image registration module 120 registers the intraoral images that have been processed by the foreign object identifier 115 using one or more image registration techniques. For example, image registration module 120 may perform image registration using modified intraoral images in which representations of foreign objects have been removed from the intraoral images. After image registration is complete, or as image registration is performed, model generation module 125 generates a 3D virtual model of the imaged dental site.

A user interface 140 may function during an intraoral scan session. As scanner 150 generates intraoral images and those intraoral images are processed by foreign object identifier 115, a view screen showing a two-dimensional (2D) or 3D representation of a scanned dental site may be output to a display (e.g., of computing device 105). Foreign objects that have been filtered out by foreign object identifier 115 may not be shown in the 2D or 3D representation. Images may be stitched together during the intraoral scan session to continuously update the representation of the dental site during the intraoral scan session. Image registration processes and model generation processes may be performed similar to those performed by image registration module 120 and model generation module 125, except more quickly and with lower accuracy. The representation of the dental site may show a user of the scanner 150 what areas have been sufficiently imaged and which areas would benefit from further imaging.

In some instances, foreign object identifier 115 may be unable to accurately determine whether an object at a dental site is a foreign object or a native object. In such instances, the foreign object identifier 115 may or may not filter out the foreign object. If the foreign object is filtered out, then the user interface may still show an outline, black and white representation, translucent representation, mesh representation, or other non-standard representation of the foreign object in the view screen. A user may then select the representation of the foreign object shown in the view screen and be presented with an option to proceed with filtering out the foreign object or to add the foreign object back to the intraoral images. If the user selects to filter out the foreign object, then the outline or other non-standard representation of the foreign object may be removed from the view screen. Additionally, data (e.g., physical properties) about the foreign object may be added to an entry for a reference object 130. Future scans of the same patient and/or different patients may then use the new reference object 130 and the data associated with it to successfully identify additional instances of the foreign object. Therefore, the accuracy of the foreign object identifier may continually improve. If the user selects not to filter out the foreign object, then the foreign object may be added back to the intraoral image (or the original intraoral image may have been kept and may be used rather than the modified version of the intraoral image). If the user fails to select the foreign object, then the original decision to filter out the foreign object may stand. In such instances, a new reference object may or may not be added to data store 110 for the foreign object.

If the foreign object was not originally filtered out, then the foreign object will be shown in the view screen in the same manner as other features and objects of the dental site. However, the foreign object may be outlined, highlighted, or otherwise emphasized. The user may then select the foreign object representation in the view screen and be presented with an option to filter out the foreign object or to leave the foreign object in the intraoral images. If the user selects to filter out the foreign object, then the foreign object may be removed from intraoral images of the intraoral scan that depict the foreign object. Additionally, data (e.g., physical properties) about the foreign object may be added to an entry for a reference object 130. Future scans of the same patient and/or different patients may then use the new reference object 130 and the data associated with it to successfully identify additional instances of the foreign object. Therefore, the accuracy of the foreign object identifier may continually improve. If the user selects to leave the foreign object (likely indicating that the foreign object is in fact a native object rather than a foreign object), then the intraoral images that include representations of that object may be unmodified and the outline or other emphasis of that object in the view screen may be removed. If the user fails to select the foreign object, then the original decision to leave the foreign object may stand.

In some instances, foreign objects may be intentionally added to the patient's mouth for imaging and/or dentistry or orthodontia. In such instances, the foreign object identifier 115 may not filter out representations of the foreign object (which may be a reference object). Instead, foreign object identifier 115 may identify the foreign object and then use known physical properties of the foreign object (e.g., such as shape, color, etc.) to augment the image with further information about the foreign object. Additionally, or alternatively, the known properties of the foreign object may be used to augment a virtual 3D model generated from or otherwise associated with the image. For example, a user may desire to scan the foreign object to obtain an accurate and complete representation of the foreign object, but the foreign object may have a geometry that is difficult to fully capture and/or be made of a material that is difficult to image (e.g., such as titanium). Once the foreign object identifier 115 identifies the foreign object as matching a known reference object 130, foreign object identifier 115 may use the known physical properties of the reference object to improve the representation of the foreign object in the intraoral images and/or in virtual 3D models. For example, the position and orientation of the foreign object in the image may be determined, and this position and orientation may be used to add data (e.g., shape data or surface data) for the foreign object to the image and/or virtual 3D model. This process may be useful, for example, for foreign objects such as scan bodies, braces, and so on.

Once a foreign object is identified that is to be augmented using a reference object 130, information about the foreign object may additionally be added to the view screen by user interface 140. For example, if a user scans an edge of a scan body and that scan body is then identified as matching a reference object 130, then unscanned portions of the scan body may be registered with and shown at a correct position and orientation relative to other features on the dental site in the view screen. The additional unscanned portions of the scan body may be shown in mesh or an outline, for example. This may show a user additional images to be taken to gather sufficient images to fully capture the foreign object. As new images are generated, the mesh or outline representation of the foreign object may be replaced with actual scan data for the foreign object. If ultimately there are any regions that a user is unable to image successfully, then the information from the reference object 130 may be used to fill in the missing information. Such filled in missing information may be filled in on the intraoral images and/or on a virtual 3D model generated from or otherwise associated with the intraoral images.

FIGS. 1B-9 illustrate methods associated with intraoral scanning as well as identification and processing of foreign objects in intraoral images generated during the intraoral scanning. The methods may be performed by processing logic that comprises hardware (e.g., circuitry, dedicated logic, programmable logic, microcode, etc.), software (such as instructions run on a processing device), or a combination thereof. Various embodiments may be performed by processing logic executing on computing device 105 of FIG. 1A. The methods may be performed in real-time or near real-time as images are generated by a scanner and/or received from the scanner.

Figure 1B:
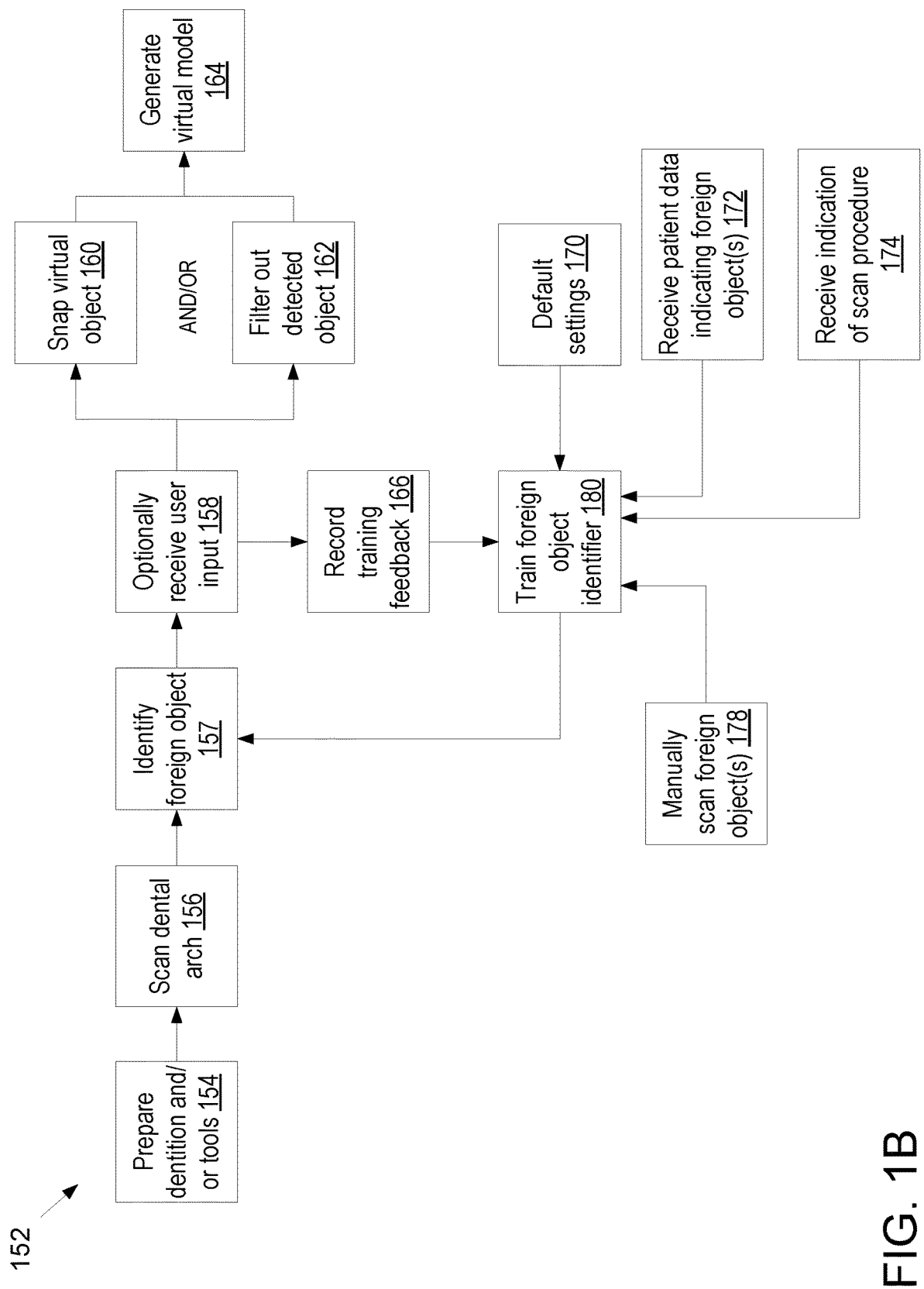
FIG. 1B illustrates a flow diagram for a method of identifying representations of foreign objects in intraoral images, in accordance with embodiments of the present disclosure.

FIG. 1B illustrates a flow diagram for a method 152 of identifying representations of foreign objects in intraoral images, in accordance with embodiments of the present disclosure. At block 154, regions of a patient's dentition and/or mouth and/or one or more tools may be prepared for intraoral scanning. The preparation of the dentition and/or mouth may include spraying such regions with a dye having a color that is not natively found inside of a patient's mouth. For example, a patient's tongue may be spray coated, a region of a patient's dental arch that is not to be scanned may be spray coated, and so on. Similarly, one or more tools that will be inserted into the patient's mouth may be spray coated. Some tools may already be a particular color that does not naturally occur in the patient's mouth. For example, a dentist may put on gloves having a same color as the dye in the spray coating.

At block 156, a dental practitioner scans a dental arch (or a portion of a dental arch) using scanner 150 of FIG. 1A. At block 157, processing logic processes one or more intraoral images from the intraoral scan to identify any foreign objects. The intraoral images may be the intraoral images included in scan data generated by the scanner 150. Alternatively, a 3D model may be generated from intraoral images generated by the scanner 150. The 3D model may then be projected onto a 2D surface to generate a new image that potentially includes data from multiple intraoral images generated by scanner 150. The new image may be processed to identify any foreign objects in the new image. FIGS. 2-9 describe various techniques for identifying foreign objects, which may be used separately or together. At block 158, a user may be presented with an option to provide user input with regards to an identified foreign object. For example, the user may have the option of marking an identified foreign object as not being a foreign object, may have the option of marking an identified native object as being a foreign object, may have the option of confirming an identified foreign object as being a foreign object, and so on. If the user provides any user input at block 158, then at block 166 such user input is recorded. Such user input may then be used to train the foreign object identifier 115, which is described in greater detail below.

Two different operations may be performed for an identified foreign object. In a first operation, a virtual object (e.g., a virtual 3D model or other representation of the foreign object) may be added to one or more intraoral images and/or associated virtual 3D models at an appropriate location and orientation (block 160). Alternatively, the detected foreign object may be filtered out (i.e. removed) from the intraoral images (block 162). If there are more than one foreign objects detected, then the decision of whether to filter out or snap virtual objects to the detected foreign objects may be performed separately for each foreign object.

In an example of snapping a virtual object to an intraoral image and/or virtual 3D model, a bracket may be identified on a tooth of a patient. The bracket may be difficult to scan, and the image and/or 3D model of the bracket may be poor quality. However, the known data for the identified bracket may be used to complete the representation of the bracket in the image and/or virtual 3D model and to show a perfect bracket (e.g., as it is truly shaped).

At block 164, a virtual model is then generated based on the modified intraoral images (e.g., that either include additional data about the foreign object or that do not include any representations of the foreign object). In some embodiments, rather than snapping virtual objects to images (at block 160), virtual objects may be instead snapped to a virtual model constructed from one or more intraoral images based on the foreign objects identified in the one or more intraoral images. For example, intraoral images used to generate the virtual 3D model may be used to determine the position and orientation of a known object, and then that information may be used to add information about the known object to the virtual 3D model. In another example, an image may be generated by projecting the virtual 3D model onto a 2D surface, and that image may be processed to identify the known object therein and to determine the position and orientation of the known object. The determined position and orientation of the known object may then be used to add information about the known object to the virtual 3D model. Alternatively, the virtual object may be snapped both to the intraoral images and to the virtual 3D model.

As mentioned, at block 180 processing logic may train the foreign object identifier to better identify foreign objects in intraoral images. The foreign object identifier may be trained using data from numerous different sources. In some embodiments, the foreign object identifier comes pre-trained with default settings 170. Such default settings may include global color data (or other wavelength reflectivity, wavelength reactivity, wavelength refraction, etc.) for colors that are commonly found in the mouth and/or that are not found in the mouth. Such default settings may further include textures, patterns, shapes, etc. that are commonly found in the mouth and/or that are not found in the mouth. In one example, a default reference object library may be pre-populated with data for a plurality of common dental tools. Each entry in the default reference object library may include information such as a virtual 3D model, shape information, color information, surface pattern information, texture information, etc. about a particular dental tool.

In some embodiments, at block 172 the foreign object identifier may receive patient data indicating one or more foreign objects that are included in a particular patient's mouth (e.g., specific brackets attached to the patient's teeth). This may narrow the field of foreign objects to search for, and search criteria and/or search boundaries may be adjusted to account for the fact that there is a 100% chance that the indicated foreign object(s) are in the mouth. The foreign objects may be indicated based on a user scanning a bar code, manually entering a code or product identifier, selecting a foreign object from a drop down menu, and so on. Based on the provided information, the foreign object may be identified in a reference object library, and physical properties to search for intraoral images may be determined.

In some embodiments, at block 174 the foreign object identifier may receive an indication of a particular scan procedure that was performed. For example, some types of scan procedures may be to scan for particular information. For example, a retainer scan procedure may be performed to scan a patient's mouth to depict a retainer on the patient's dentition. A retainer scan procedure may include retrieving or looking up bracket information (e.g., from a reference object library. Similarly, a restorative scan procedure may include retrieving or looking up restorative object information (e.g., from a reference object library). The foreign object identifier may then adjust its parameters to find brackets (in the instance of a retainer scan procedure) or to find a restorative object (in the instance of a restorative scan procedure).

In some embodiments, at block 178 a training mode may be entered. While the foreign object identifier is in the training mode, a user may use scanner 150 to generate a 3D scan of a foreign object. This may include generating a series of 3D images and/or a 3D video of the object. The images and/or video may then be used to generate a virtual 3D model of the object. Additionally, one or more image processing algorithms may be applied to the images and/or video to determine one or more physical properties of the object. The images, video, virtual 3D model and/or physical properties may then be added to a new entry for the foreign object in a reference object library.

Once the foreign object identifier is trained, it may more accurately identify specific foreign objects at block 157.

Figure 2:
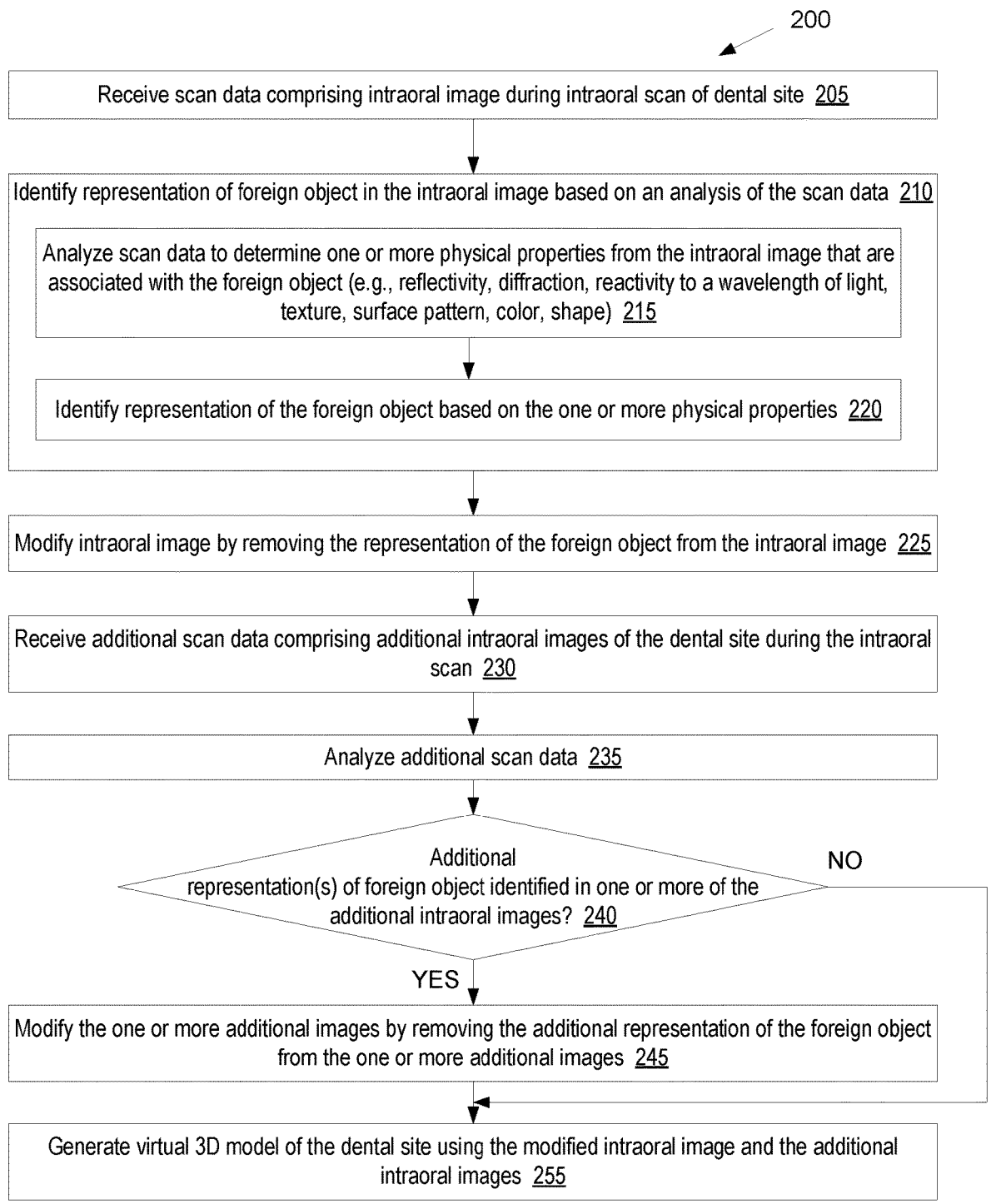
FIG. 2 illustrates a flow diagram for a method of filtering representations of foreign objects out of intraoral images, in accordance with embodiments of the present disclosure.

FIG. 2 illustrates a flow diagram for a method 200 of filtering representations of foreign objects out of intraoral images, in accordance with embodiments of the present disclosure. A dental practitioner may perform an intraoral scan of a dental site (e.g., of upper and/or lower dental arches, portions of an upper and/or lower dental arch, etc.). During the intraoral scan or after the intraoral scan is complete, processing logic may receive scan data comprising one or more intraoral images of the dental site at block 205 of method 200. Each intraoral image may be a three dimensional (3D) image generated by an intraoral scanner (e.g., scanner 150 of FIG. 1).

At block 210, processing logic analyzes the scan data and identifies a representation of a foreign object in the intraoral image based on the analysis. In some embodiments, analyzing the scan data includes processing one or more intraoral images in the scan data using one or more image processing algorithms. Examples of image processing algorithms that may be used to process an intraoral image include edge detection algorithms, 3D object detection algorithms, feature extraction algorithms (e.g., speeded up robust features (SURF) algorithm, scale-invariant feature transform (SIFT) algorithm, Haar-like features algorithm, histogram of oriented gradients (HOG) algorithm, etc.), and so on. After the intraoral image is processed, shapes, edges, features, and so on may be determined for the intraoral image. The shapes, edges, features, etc. may then be further analyzed to identify native objects and foreign objects. In an example, foreign objects may often have a uniform surface pattern and/or texture on at least a portion of the foreign objects. Such uniform surface pattern and/or texture may be used to determine a contour of the foreign object, where the contour extends around the region with the uniform surface pattern and/or texture.

In one embodiment, at block 215 processing logic analyzes the scan data to determine one or more physical properties represented in the intraoral image. This may include analyzing the intraoral image before or after any of the above mentioned image processing algorithms have been used on the intraoral image. Multiple different types of physical properties may be detected, including reflectivity, diffraction, reactivity to a wavelength of light, texture, surface pattern, color and/or shape. Other physical properties and/or optical properties may also be detected.

In some instances, a foreign object may be identified based solely on a single physical property (e.g., based on color). For example, dental instruments, a dentist's gloves, cotton rolls, etc. may all be dyed a color that is not naturally occurring in the mouth. For example, the color blue does not generally occur naturally in the teeth or gums. Accordingly, a hue of blue may be used. Additionally, a dental practitioner may spray objects that will be inserted into the mouth with a dye having a color that is not naturally occurring in the mouth. The dental practitioner may also spray a patient's tongue with the dye so that the tongue will be identified as a foreign object based on its color. Any region of the intraoral image having the non-natural color can easily be identified as belonging to a foreign object with minimal processing. A simple color filter may be applied to intraoral images, for example, which filters out one or more colors (e.g., a range of colors) that are not naturally occurring in the mouth.

In some instances, a combination of physical properties of an object may be used to identify that object as a foreign object. For example, the shape of an object and that objects surface pattern or texture may be used together to identify the foreign object. The more physical properties that can be identified about an object, the easier it may be to determine whether or not that object is a foreign or native object, and the more accurate that determination may be.

For the reactivity to a wavelength of light data, a specific wavelength of light may have been shined on a dental site while the intraoral image was generated. One example of a wavelength of light that may be used is near infrared (NIR) light. Other examples include IR light, ultraviolet (UV) light, near ultraviolet (NUV) light, mid infrared (MIR) light, far infrared (FIR) light, extreme ultraviolet (EUV) light, extreme high frequency (EHF) electromagnetic radiation, and so on. Native objects of the dental site may react to the wavelength of light in one manner, and foreign objects at the dental site may react to the wavelength of light in a different manner. For example, teeth and tissue in the mouth may have particular reflections to NIR light, and metal objects may have very different reflections to NIR light. For example, foreign objects would typically appear very dark to NIR light as compared to teeth and tissue. Additionally, blood and saliva may have different reflectances to NIR light than teeth and tissue, and the use of NIR light may be used to detect blood and/or saliva in intraoral images. Such blood and/or saliva may be identified as a foreign object in some embodiments.

In one embodiment, processing logic identifies bubbles in the intraoral image. Bubbles may be signs of saliva, and generally do not occur as part of a tooth or gingival tissue. Accordingly, the presence of bubbles may be another physical property that may be detected and used to identify saliva and/or blood.

At block 220, processing logic identifies the representation of the foreign object as belonging to a foreign object based on the one or more physical properties (e.g., based on reflectivity, diffraction, reactivity to a wavelength of light, texture, surface pattern, color and/or shape). This may include comparing the identified physical properties to physical properties of one or more reference objects in a reference object library. If a match is found between one or more physical properties of an object in the intraoral image and one or more physical properties of a reference object, then the representation of the object may be identified as a foreign object.

At block 225, processing logic modifies the intraoral image by removing the representation of the foreign object from the intraoral image. At block 230, processing logic receives additional scan data comprising additional intraoral images of the dental site during the intraoral scan. These intraoral images could have been received together with the first intraoral image initially before the operations of block 210 were performed. Alternatively, one or more additional images may be received after the initial image was received and while (or after) the operations of block 210 and/or 225 are being performed on the first intraoral image.

At block 235, processing logic analyzes the additional scan data in the same manner as described with reference to block 210. At block 240, processing logic then determines whether any of the additional intraoral images include a representation of the foreign object. If so, then those additional images are also modified at block 245 by removing the foreign object from the additional intraoral images. Otherwise the method proceeds to block 255.

At block 255, processing logic registers (i.e., "stitches") together) the intraoral images. This may include registering a first modified intraoral image to a second modified intraoral image, or registering a first modified intraoral image to a second unmodified intraoral image, for example. In one embodiment, performing image registration includes capturing 3D data of various points of a surface in multiple images, and registering the images by computing transformations between the images. The images may then be integrated into a common reference frame by applying appropriate transformations to points of each registered image. Processing logic then generates a virtual 3D model of the dental site based on the registration using the modified intraoral image and the additional intraoral images (which may or may not be modified). The virtual 3D model may be a digital model showing the surface features of the dental site.

Figure 3:
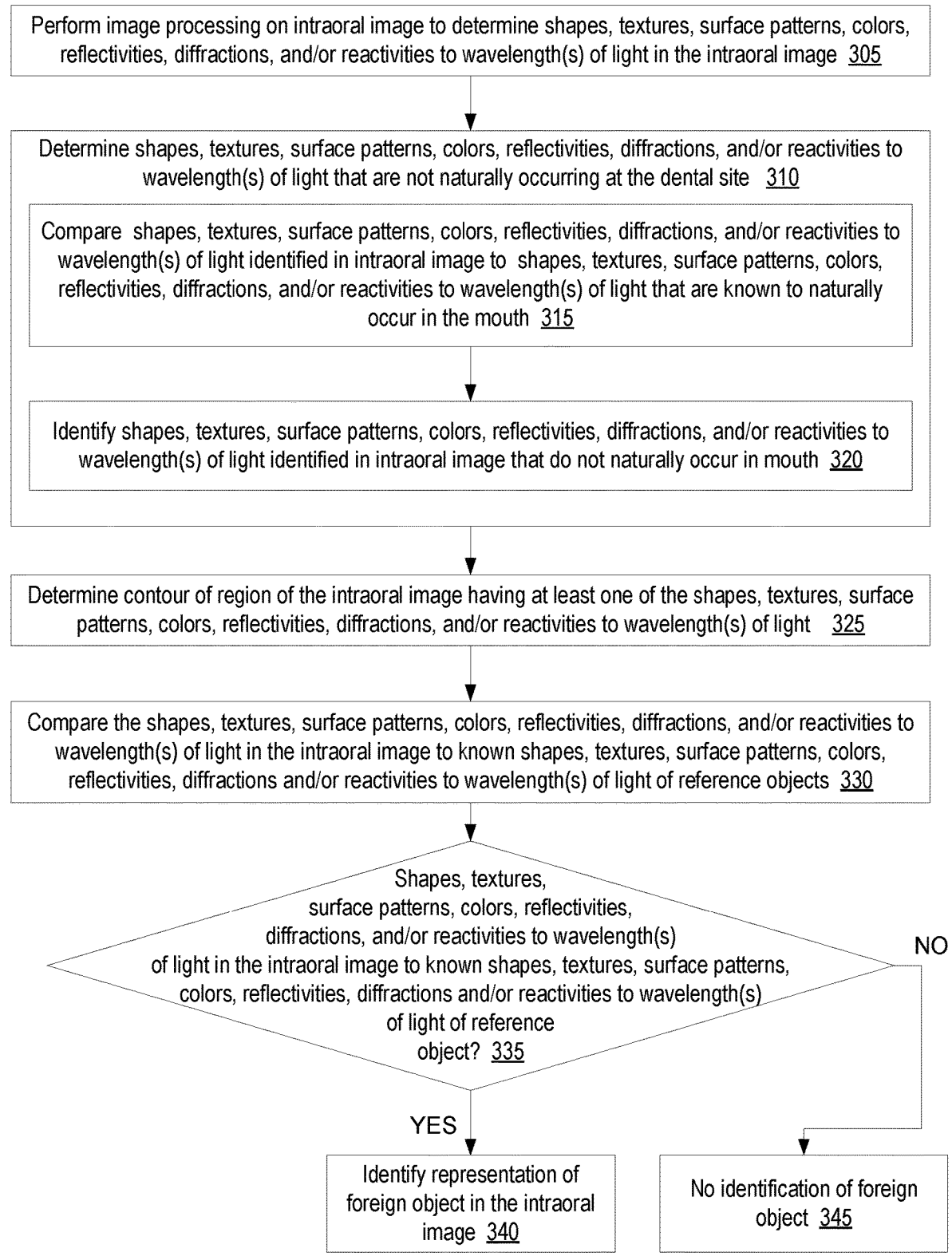
FIG. 3 illustrates a flow diagram for a method of identifying foreign objects in intraoral images, in accordance with embodiments of the present disclosure.

FIG. 3 illustrates a flow diagram for a method 300 of identifying foreign objects in intraoral images, in accordance with embodiments of the present disclosure. At block 305 of method 300, processing logic performs image processing on an intraoral image to determine shapes, textures, surface patterns, colors, reflectivities, diffractions and/or reactivities to wavelengths of light in the intraoral image. The image processing may be performed using edge detection algorithms, feature extraction algorithms and/or other image processing algorithms, such as those described above.

At block 310, processing logic determines shapes, textures, surface patterns, colors, reflectivities, diffractions and/or reactivities to wavelengths of light from the intraoral image that are not naturally occurring at a dental site. This may include at block 315 comparing the shapes, textures, surface patterns, colors, reflectivities, diffractions and/or reactivities to wavelengths of light identified in the intraoral image to shapes, textures, surface patterns, colors, reflectivities, diffractions and/or reactivities to wavelengths of light that are known to naturally occur in the mouth. At block 320, processing logic may then identify shapes, textures, surface patterns, colors, reflectivities, diffractions and/or reactivities to wavelengths of light from the intraoral image that do not naturally occur in the mouth based on the comparison.

At block 325, processing logic determines a contour of a region of the intraoral image having at least one of the shapes, textures, surface patterns, colors, reflectivities, diffractions and/or reactivities to wavelengths of light that were determined to not natively occur in the mouth. At block 330, processing logic may compare the contour, shapes, textures, surface patterns, colors, reflectivities, diffractions and/or reactivities to wavelengths of light in the intraoral image to known shapes, textures, surface patterns, colors, reflectivities, diffractions and/or reactivities to wavelengths of light of reference objects. At block 335, processing logic may determine whether the shapes, textures, surface patterns, colors, reflectivities, diffractions and/or reactivities to wavelengths of light in the intraoral image match shapes, textures, surface patterns, colors, reflectivities, diffractions and/or reactivities to wavelengths of light of any known reference objects in view of the comparison performed at block 330. If a match is found, the method proceeds to block 340 and the representation of the foreign object is identified. The representation of the foreign object may then be removed from the intraoral image. Note that in some embodiments, the shapes, textures, surface patterns, colors, reflectivities, diffractions and/or reactivities to wavelengths of light that are not naturally occurring in the mouth may be removed from the intraoral image at block 310 or block 325 without comparing to a library of reference objects. If no match is found at block 335, then the method continues to block 345 and no identification of a foreign object is made.

Figure 4:
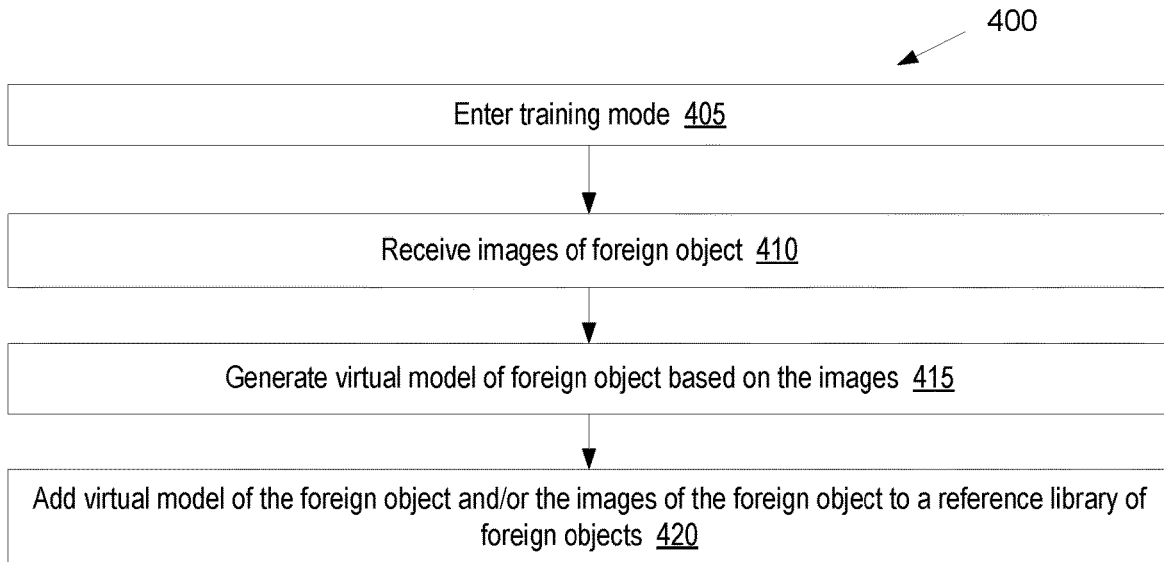
FIG. 4 illustrates a flow diagram for a method of adding an entry for a foreign object to a foreign object reference library, in accordance with embodiments of the present disclosure.

FIG. 4 illustrates a flow diagram for a method 400 of adding an entry for a foreign object to a foreign object reference library, in accordance with embodiments of the present disclosure. At block 405 of method 400, processing logic enters a training mode (e.g., based on user input). At block 410, processing logic receives one or more images of a foreign object that is to be added to a known reference object library. The images may be received during a 3D scan of the foreign object. At block 415, processing logic generates a virtual model of the foreign object based on the images. Processing logic may also perform image processing on the images and/or the virtual model to determine one or more physical properties of the foreign object. At block 420, processing logic adds the virtual model of the foreign object, the images of the foreign object and/or the physical properties of the foreign object to a reference library of foreign objects. Thereafter, representations of that object will be identified as representations of a foreign object in intraoral images.

Figure 5:
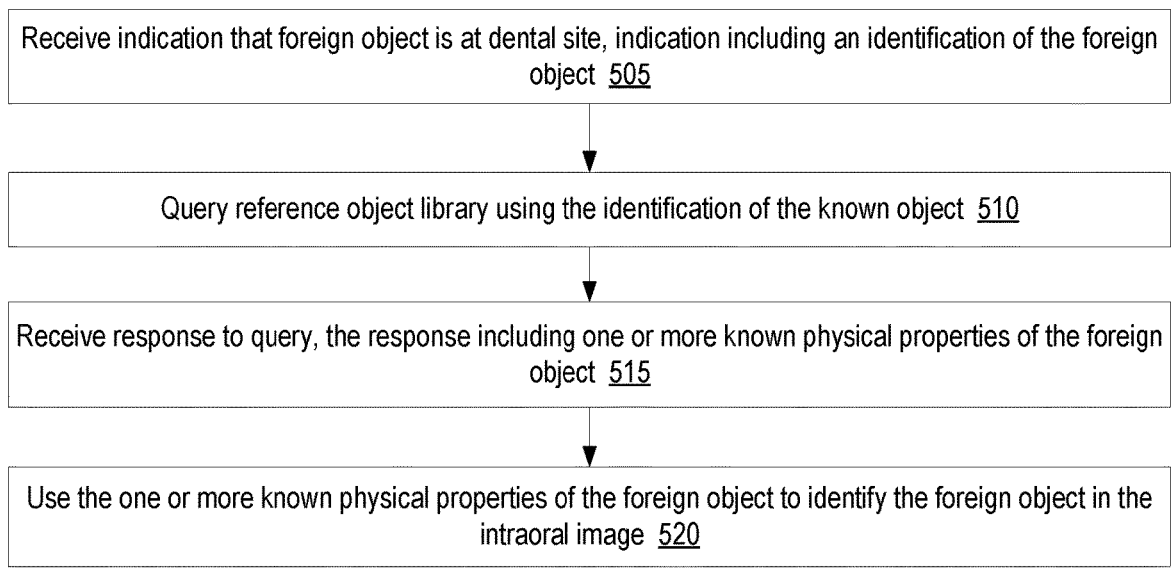
FIG. 5 illustrates a flow diagram for a method of using a foreign object reference library to identify a foreign object in an intraoral image, in accordance with embodiments of the present disclosure.

FIG. 5 illustrates a flow diagram for a method 500 of using a foreign object reference library to identify a foreign object in an intraoral image, in accordance with embodiments of the present disclosure. At block 505 of method 500, processing logic receives an indication that a foreign object is at a dental site. The indication may include an identification of the foreign object, such as by name, unique identifier, characteristics, and so on. For example, an orthodontist may indicate that a patient is wearing specific brackets for braces. At block 510, processing logic queries a reference object library using the identification of the known object. At block 515, processing logic receives a response to the query. The response may include one or more physical properties of the foreign object, a virtual model of the foreign object, metadata associated with an entry of the foreign object, and/or other information. At block 520, processing logic uses the one or more known properties of the foreign object to identify the foreign object in the intraoral image. For example, processing logic may search the intraoral image for objects having the physical properties identified in the response.

Figure 6:
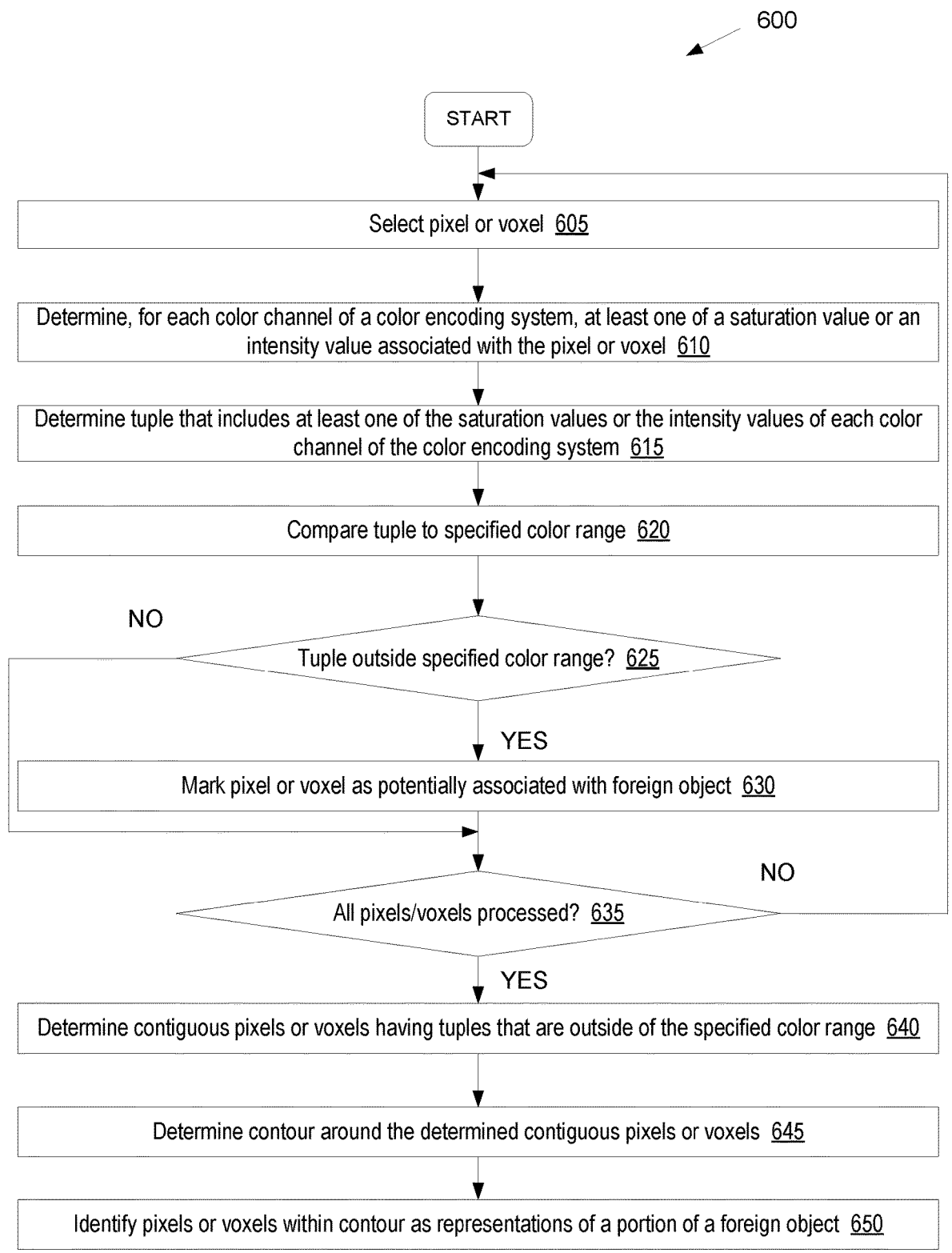
FIG. 6 illustrates a flow diagram for a method of identifying foreign objects in intraoral images based on color, in accordance with embodiments of the present disclosure.

FIG. 6 illustrates a flow diagram for a method 600 of identifying foreign objects in intraoral images based on color, in accordance with embodiments of the present disclosure. At block 605 of method 600, processing logic selects a pixel (or voxel) in an intraoral image. At block 610, processing logic determines, for each color channel of a color encoding system, at least one of a saturation value or an intensity value associated with the pixel (or voxel). At block 615, processing logic determines a tuple that includes at least one of the saturation values or the intensity values of each color channel of the color encoding system. For example, if the RGB color encoding system is used, then the tuple may be a 3-tuple (r, g, b).

At block 620, processing logic compares the generated tuple to a specified color range. The specified color range may cover some or all naturally occurring colors in the mouth. Alternatively, the specified color range may cover some or all colors not naturally occurring in the mouth. At block 625, processing logic determines whether the tuple is outside of the color range (in the case where the color range indicates colors naturally occurring in the mouth). If the tuple is outside of the color range (in the case where the color range indicates colors naturally occurring in the mouth), the method continues to block 630, and the pixel (or voxel) is marked as being potentially associated with a foreign object. If the tuple is inside of the color range, the method proceeds to block 635.

Alternatively, at block 625 processing logic may determine whether the tuple is inside of the color range (in the case where the color range indicates colors not naturally occurring in the mouth). If the tuple is inside of the color range (in the case where the color range indicates colors not naturally occurring in the mouth), the method continues to block 630, and the pixel (or voxel) is marked as being potentially associated with a foreign object. If the tuple is outside of the color range, the method proceeds to block 635.

At block 635, processing logic determines whether all pixels of the intraoral image have been processed. If there are further pixels to process, the method returns to block 605 and another pixel is selected for analysis. If all pixels of the intraoral image have been processed, the method continues to block 640. At block 640, processing logic determines contiguous pixels or voxels having tuples that are outside of the specified color range (in the case where the color range indicates colors naturally occurring in the mouth) or inside of the specified color range ((in the case where the color range indicates colors not naturally occurring in the mouth). At block 645, processing logic determines a contour around the determined contiguous pixels or voxels. At block 650, processing logic identifies the pixels or voxels within the contour as representations of a portion of a foreign object. Alternatively, the operations of blocks 640-645 may be omitted. Instead, all pixels marked as potentially associated with a foreign object may be filtered out of the intraoral image.

Figure 7:
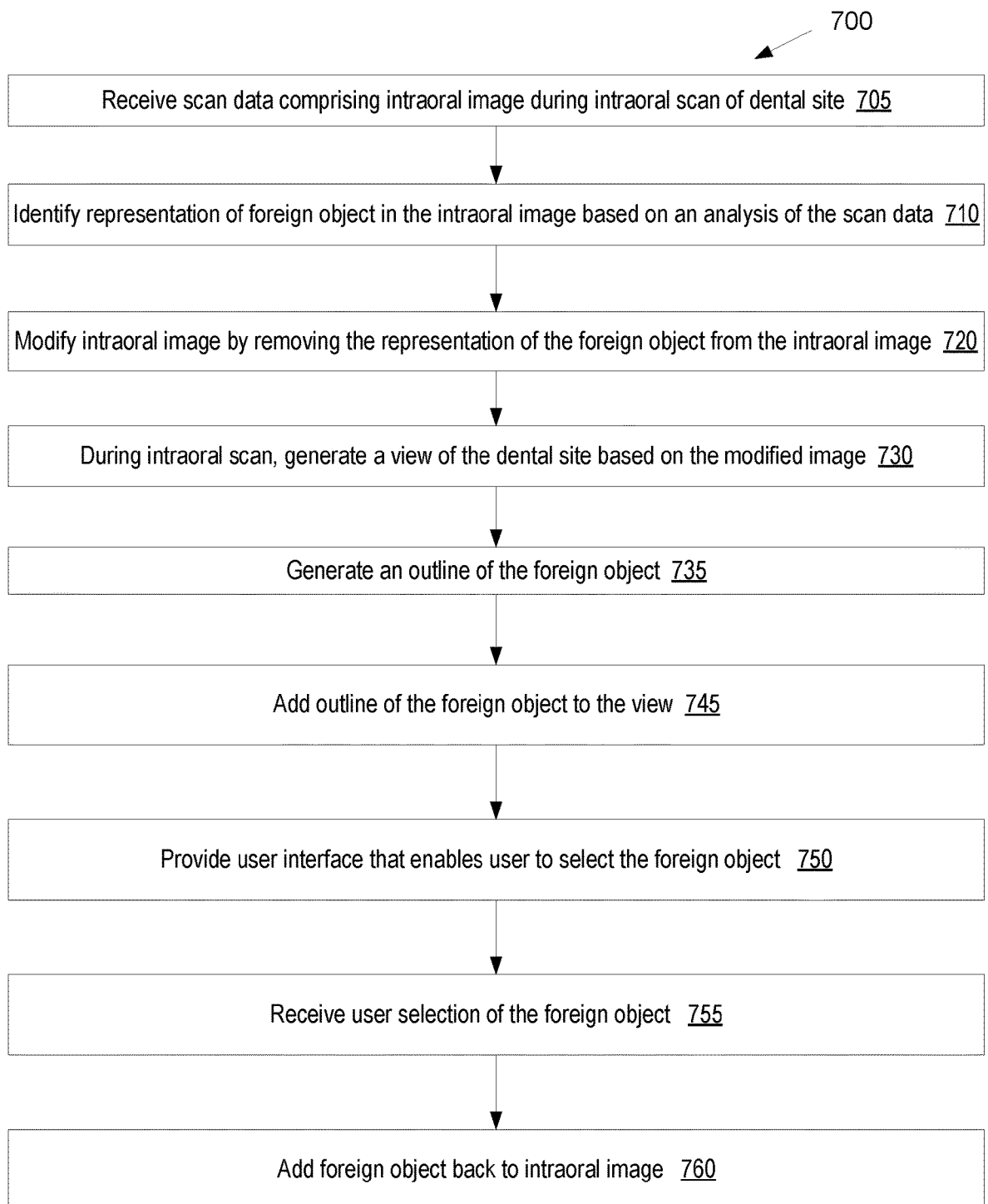
FIG. 7 illustrates a flow diagram for a method of providing a user interface for management of foreign objects in intraoral images, in accordance with embodiments of the present disclosure.

FIG. 7 illustrates a flow diagram for a method 700 of providing a user interface for management of foreign objects in intraoral images, in accordance with embodiments of the present disclosure. At block 705 of method 700, processing logic receives scan data comprising an intraoral image during an intraoral scan of a dental site. At block 710, processing logic identifies a representation of a foreign object in the intraoral image based on an analysis of the scan data. At block 720, processing logic modifies the intraoral image by removing the representation of the foreign object from the intraoral image. At block 730, during the intraoral scan, processing logic generates a view of the dental side based on the modified image.

At block 735, processing logic generates an outline, mesh representation, translucent representation, or other representation of the foreign object. At block 745, processing logic adds the outline (or other representation) of the foreign object to the view. At block 750, processing logic provides a user interface that enables a user to select the foreign object. At block 755, processing logic receives a user selection of the foreign object. The user selection indicates that the object should not be removed from the intraoral image (e.g., may identify the object as a native object). At block 760, processing logic adds the foreign object back to the intraoral image.

Figure 8:
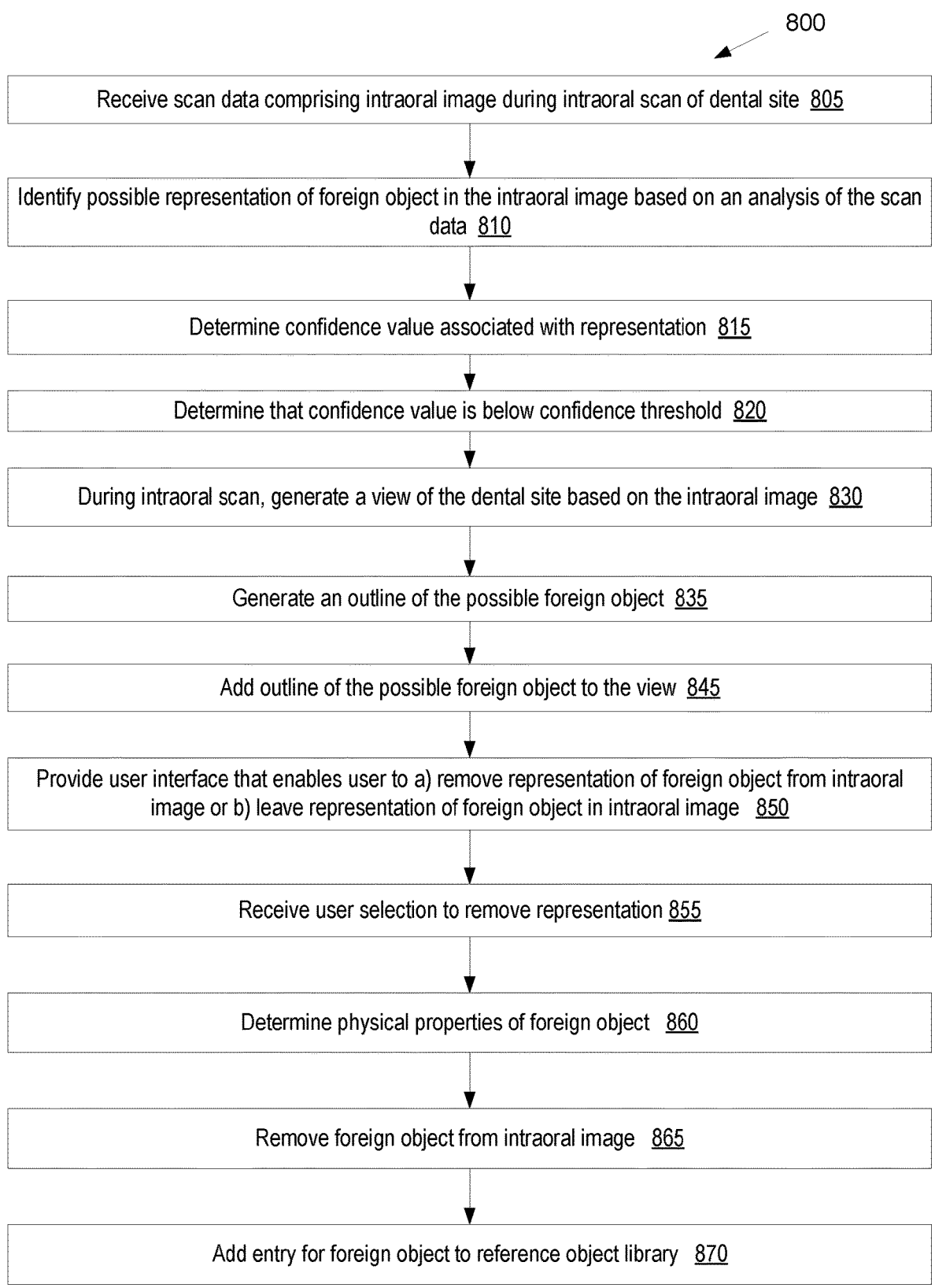
FIG. 8 illustrates a flow diagram for a further method of providing a user interface for management of foreign objects in intraoral images, in accordance with embodiments of the present disclosure.

FIG. 8 illustrates a flow diagram for a further method 800 of providing a user interface for management of foreign objects in intraoral images, in accordance with embodiments of the present disclosure. At block 805 of method 800, processing logic receives scan data comprising an intraoral image during an intraoral scan of a dental site. At block 810, processing logic identifies a representation of a foreign object in the intraoral image based on an analysis of the scan data. At block 815, processing logic determines a confidence value associated with the representation. At block 820, processing logic determines that the confidence value is below a threshold. If the confidence value is below the threshold, this indicates that processing logic is unable to accurately determine whether or not the identified object should be classified as a foreign object or a native object.

At block 830, during the intraoral scan, processing logic generates a view of the dental side based on the modified image. At block 835, processing logic generates an outline, mesh representation, translucent representation, or other representation of the possible foreign object. At block 845, processing logic adds the outline (or other representation) of the foreign object to the view. At block 850, processing logic provides a user interface that enables a user to a) remove the representation of the foreign object from the intraoral image or b) leave the representation of the object in the intraoral image.

At block 855, processing logic receives a user selection to remove the representation from the intraoral image. At block 860, processing logic determines one or more physical properties of the foreign object. At block 865, processing logic removes the foreign object from the intraoral image. At block 870, processing logic adds an entry for the foreign object to a reference object library. The entry may include the determined physical properties of the foreign object. In future intraoral images the processing logic will then be able to identify the foreign object with increased confidence and accuracy.

In some embodiments, machine learning models such as convolutional neural networks (CNNs) are used to identify foreign objects in intraoral images. The intraoral images may be images generated by an intraoral scanner and/or images generated by projecting a virtual 3D model of a dental site onto a 2D surface or plane. The machine learning models may alternatively, or additionally, identify foreign objects in virtual 3D models directly (e.g., by inputting data representing the virtual 3D models into the machine learning models). In one example embodiment, a method of training a machine learning model includes receiving a training dataset comprising a plurality of intraoral images, each image of the plurality of intraoral images comprising a depiction of a dental site and a label indicating whether or not the intraoral image includes a foreign object therein. Intraoral images that include a foreign object may further include a provided contour of the foreign object. The intraoral images may be real images and/or may be computer generated images. The provided contours may have been generated using a manual process in which a user has drawn the contours around foreign objects in the images or an automated or semi-automated process. In some embodiments, intraoral images with foreign objects are further labeled with a class, type or category of the foreign object. Each type of foreign object may be accompanied by an appropriate label, for example.

Training the machine learning model includes inputting the training dataset into an untrained machine learning model (e.g., CNN or other neural network) and training the untrained machine learning model based on the training dataset to generate a trained machine learning model that identifies foreign objects in intraoral images. The machine learning model may also be trained to generate a contour of the foreign object. In one embodiment, the machine learning model is trained to generate a binary mask, where a first value of the binary mask indicates pixels that are associated with foreign objects and a second value of the binary mask indicates pixels that are associated with native objects. Additionally, for an input image the trained machine learning model may output an indication of a type of foreign object that has been identified in the intraoral image.

Processing logic processes images from the training dataset one at a time generally. Processing logic processes the intraoral image to determine an output (a classification or label) and compares the determined classification or label (or multiple classifications or labels) to the provided classification(s) or label(s) associated with the intraoral image to determine one or more classification error. An error term or delta may be determined for each node in the artificial neural network. Based on this error, the artificial neural network adjusts one or more of its parameters for one or more of its nodes (the weights for one or more inputs of a node). Parameters may be updated in a back propagation manner, such that nodes at a highest layer are updated first, followed by nodes at a next layer, and so on. An artificial neural network contains multiple layers of "neurons", where each layer receives as input values from neurons at a previous layer. The parameters for each neuron include weights associated with the values that are received from each of the neurons at a previous layer. Accordingly, adjusting the parameters may include adjusting the weights assigned to each of the inputs for one or more neurons at one or more layers in the artificial neural network.

In some embodiments, an initial machine learning model is initially trained using a small dataset with manually labeled and contoured foreign objects. This machine learning model may then be used to automatically define contours around foreign objects in additional images in a training dataset that will be used to train a more accurate machine learning model (or to further train the initial machine learning model). The contours generated for images in the training dataset may be reviewed by a user, and may be corrected by the user where they are incorrect. The extended dataset may then be used to train a final model to define contours around foreign objects in intraoral images and to identify foreign objects in intraoral images. This iterative process of generating the machine learning model that defines contours around foreign objects makes it possible to prepare a large training dataset with minimal user time spent annotating images.

Figure 9:
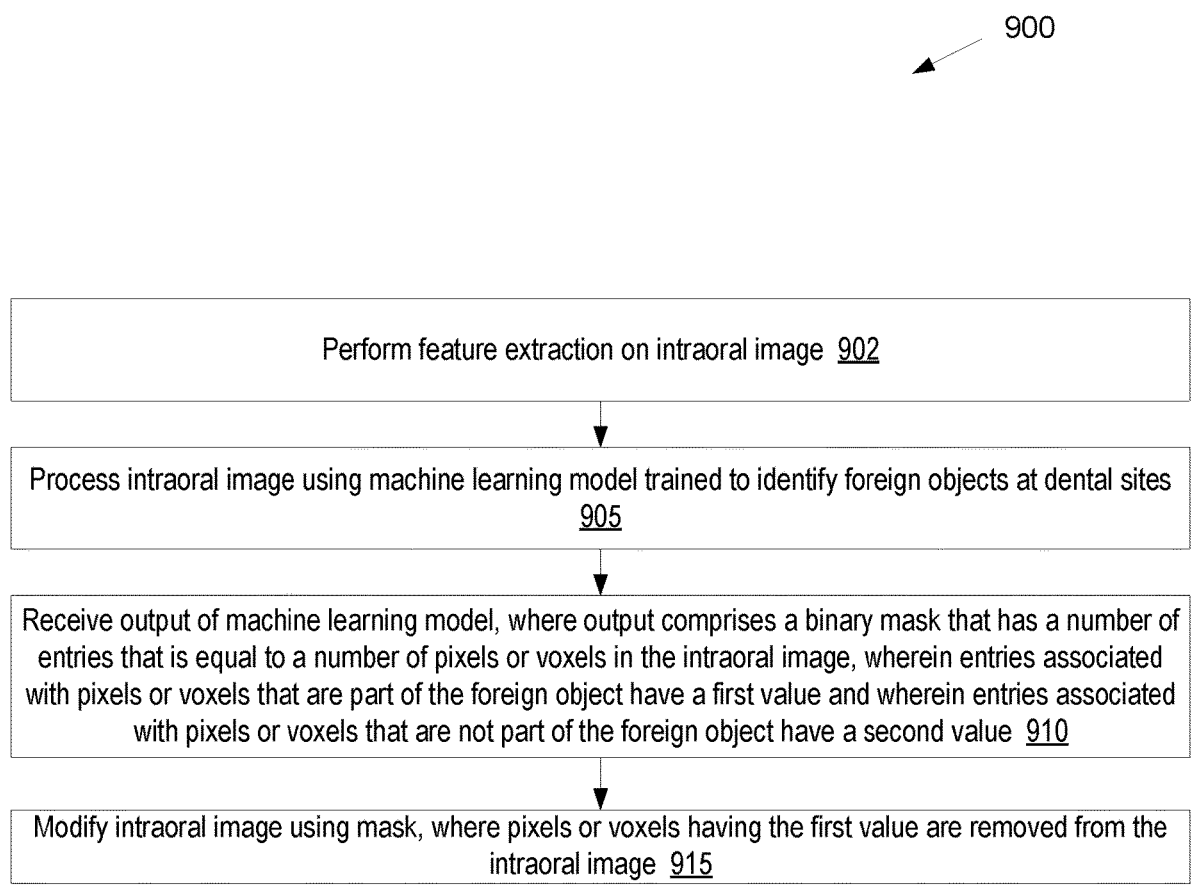
FIG. 9 illustrates a flow diagram for a method of filtering representations of foreign objects out of intraoral images based on use of a trained machine learning model, in accordance with embodiments of the present disclosure.

FIG. 9 illustrates a flow diagram for a method 900 of filtering representations of foreign objects out of intraoral images based on use of a trained machine learning model (e.g., a deep learning model, artificial neural network, convolutional neural network, etc.), in accordance with embodiments of the present disclosure. At block 902 of method 900, processing logic may perform feature extraction on an intraoral image to determine features in the image. This may include performing edge detection, object detection, and/or other feature extraction techniques described herein above.

At block 905, processing logic processes the intraoral image (and/or the extracted features of the intraoral image) using a trained machine learning model. In one embodiment, the trained machine learning model is a deep neural network. In one embodiment, the trained machine learning model is a CNN. A convolutional neural network (CNN), for example, hosts multiple layers of convolutional filters. Pooling is performed, and non-linearities may be addressed, at lower layers, on top of which a multi-layer perceptron is commonly appended, mapping top layer features extracted by the convolutional layers to decisions (e.g. classification outputs). Deep learning is a class of machine learning algorithms that use a cascade of multiple layers of nonlinear processing units for feature extraction and transformation. Each successive layer uses the output from the previous layer as input. Deep neural networks may learn in a supervised (e.g., classification) and/or unsupervised (e.g., pattern analysis) manner. Deep neural networks include a hierarchy of layers, where the different layers learn different levels of representations that correspond to different levels of abstraction. In deep learning, each level learns to transform its input data into a slightly more abstract and composite representation. In an image recognition application, for example, the raw input may be a matrix of pixels; the first representational layer may abstract the pixels and encode edges; the second layer may compose and encode arrangements of edges; the third layer may encode higher level shapes (e.g., teeth, lips, gums, etc.); and the fourth layer may recognize that the image contains a face or define a contour around a foreign object in the image. Notably, a deep learning process can learn which features to optimally place in which level on its own. The "deep" in "deep learning" refers to the number of layers through which the data is transformed. More precisely, deep learning systems have a substantial credit assignment path (CAP) depth. The CAP is the chain of transformations from input to output. CAPs describe potentially causal connections between input and output. For a feedforward neural network, the depth of the CAPs may be that of the network and may be the number of hidden layers plus one. For recurrent neural networks, in which a signal may propagate through a layer more than once, the CAP depth is potentially unlimited. In one embodiment, the machine learning model is a region-convolution neural network (R-CNN). An R-CNN is a type of CNN that is able to locate and detect objects in images.

The machine learning model applies a classification or label to the image based on its current parameter values. An artificial neural network includes an input layer that consists of values in a data point (e.g., RGB values of pixels in the intraoral image). The next layer is called a hidden layer, and nodes at the hidden layer each receive one or more of the input values. Each node contains parameters (e.g., weights) to apply to the input values. Each node therefore essentially inputs the input values into a multivariate function (e.g., a non-linear mathematical transformation) to produce an output value. A next layer may be another hidden layer or an output layer. In either case, the nodes at the next layer receive the output values from the nodes at the previous layer, and each node applies weights to those values and then generates its own output value. This may be performed at each layer. A final layer is the output layer, where there is one node for each class. For the artificial neural network, there may be a first class (includes foreign object) and a second class (does not include foreign object). Moreover, that class may be determined for each pixel in the image. For each pixel in the image, the final layer applies a probability that the pixel of the image belongs to the first class (foreign object) and a probability that the pixel of the image belongs to the second class (native object). In embodiments where the machine learning model has been trained to identify multiple different types of foreign objects, different classes may be determined for each pixel in the image.

At block 910, processing logic receives an output of the machine learning model. The output may include a binary mask that has a number of entries that is equal to a number of pixels or voxels in the intraoral image, wherein entries associated with pixels or voxels that are part of the foreign object have a first value and wherein entries associated with pixels or voxels that are not part of the foreign object have a second value. At block 915, processing logic modifies the intraoral image using the mask. Pixels or voxels having the first value may be removed from the intraoral image, while pixels or voxels having the second value may remain in the intraoral image.

Figure 10:
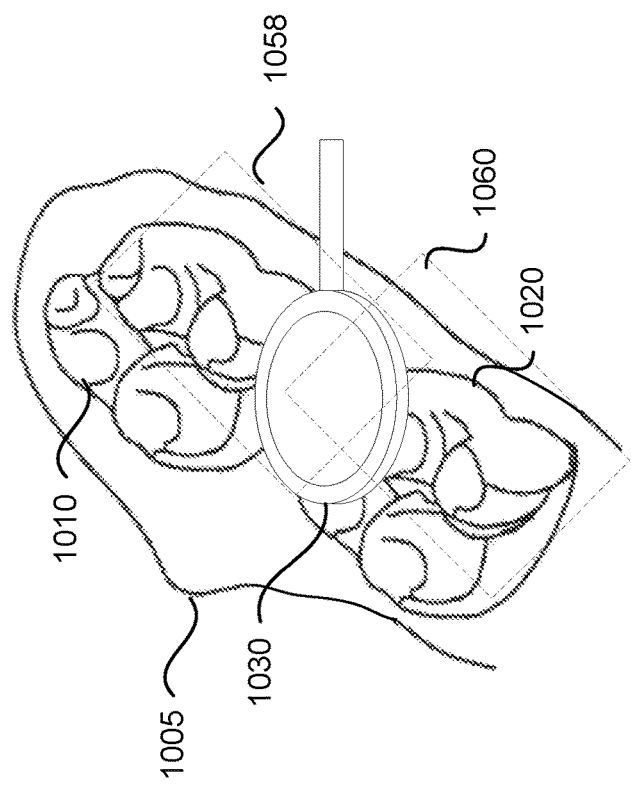
FIG. 10 illustrates a portion of an example dental arch with a foreign object disposed thereon.

FIG. 10 illustrates a portion of an example dental arch 1005 with a foreign object 1030 disposed thereon. As shown, the portion of the dental arch 1005 includes molar 1010 and molar 1020. Foreign object 1030 is a dental mirror, which is disposed at the interproximal region between molar 1010 and molar 1020. Two intraoral images 1058, 1060 have been generated of the dental arch 1005.

Figure 11:
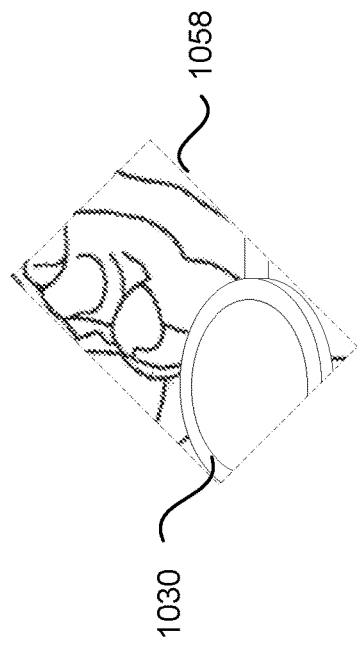
FIG. 11 illustrates a first intraoral image that includes a first representation of the foreign object, in accordance with one embodiment of the present disclosure.

FIG. 11 illustrates a first intraoral image 1058 that includes a first representation of the foreign object 1030, in accordance with one embodiment of the present disclosure. The first intraoral image 1058 may be processed using one or more of the technique described herein above to identify the foreign object 1030 in the intraoral image 1058.

Figure 12:
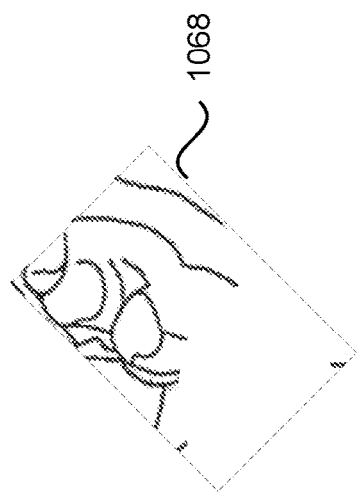
FIG. 12 illustrates a modified version of the first intraoral image of FIG. 11, where the foreign object has been filtered out in the modified version of the first intraoral image, in accordance with one embodiment of the present disclosure.

FIG. 12 illustrates a modified version 1068 of the first intraoral image of FIG. 11, where the foreign object has been filtered out in the modified version 1068 of the first intraoral image, in accordance with one embodiment of the present disclosure. The modified image 1068 may then be used to generate a virtual 3D model of the dental arch 1005. By removing the foreign object 1030 from the intraoral image 1058 prior to generating the virtual 3D model, the speed of generating the virtual model and the accuracy of the virtual model may be improved.

Note that a mirror surface of the dental mirror may include a reflection of teeth and/or gingival tissue. The reflection may show up as having physical properties of native objects in the intraoral image 158. However, the mirror surface is surrounded by a non-reflective border. In embodiments, processing logic may disregard information that is surrounded by a border having a particular shape and/or meeting other criteria. This may ensure that reflections of native features that are shown in a reflective foreign object do not confuse processing logic into incorrectly identifying a foreign object as a native object.

Figure 13B:
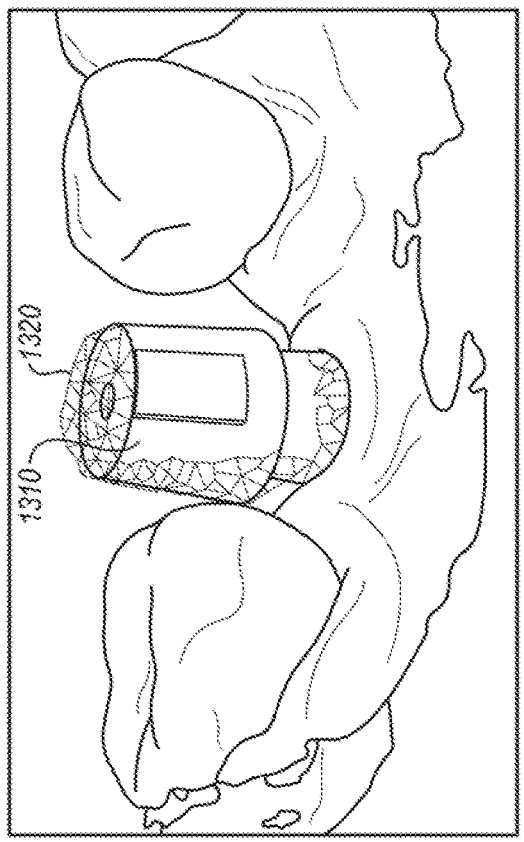
FIG. 13B illustrates the view of FIG. 13A, where not yet scanned areas of the foreign object are down, in accordance with one embodiment of the present disclosure.
Figure 13A:
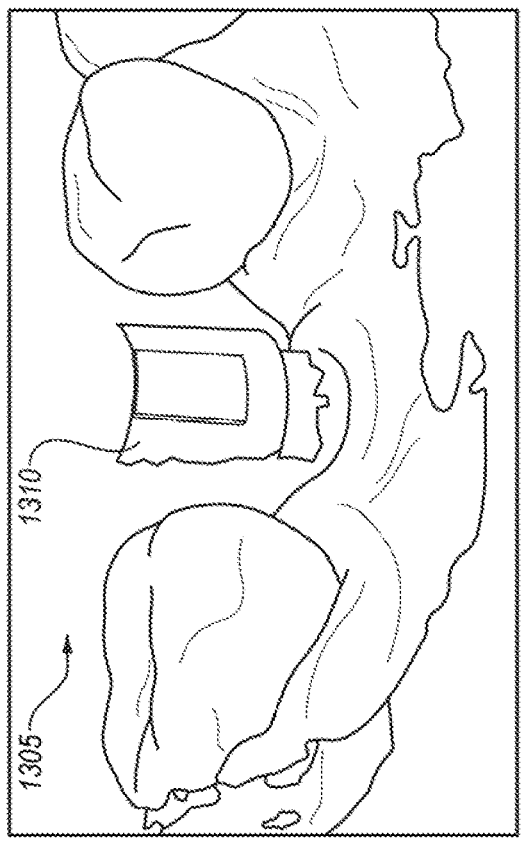
FIG. 13A illustrates view of a portion of an example dental arch with a foreign object disposed thereon, in accordance with one embodiment of the present disclosure.

FIG. 13A illustrates view of a portion of an example dental arch 1305 with a foreign object 1310 disposed thereon, in accordance with one embodiment of the present disclosure. The foreign object 1310 may be, for example, a bracket, attachment, scan body, stock implant abutment, or other permanently mounted object. The foreign object may be composed of a material that is difficult to image, such as titanium, in some embodiments.

FIG. 13B illustrates the view of FIG. 13A, where not yet scanned areas of the foreign object 1310 are shown, in accordance with one embodiment of the present disclosure. The foreign object 1310 may have been identified using any of the aforementioned techniques. Processing logic may have then snapped in a full representation of the foreign object to the view of the dental arch 1305. As shown, the not yet scanned portions of the foreign object 1310 are shown using a mesh outline. As a user generates additional intraoral images of the foreign object, the mesh outline may be filled in with image data from the additional intraoral images.

Embodiments have been discussed with reference to processing images of dental sites (e.g., intraoral images) to identify foreign objects (e.g., reference objects) therein. It should be noted that the same or similar techniques to those described herein above may be used to identify foreign objects in virtual 3D models generated by stitching together multiple intraoral images. Additionally, the images that are processed to identify foreign objects therein may have been generated by an intraoral scanner or may have been generated by projecting a virtual 3D model of a dental site onto a 2D surface or plane. Once a foreign object is identified, it may be filtered out of an image and/or virtual 3D model or may be augmented in the image and/or virtual 3D model as described above.

Figure 14:
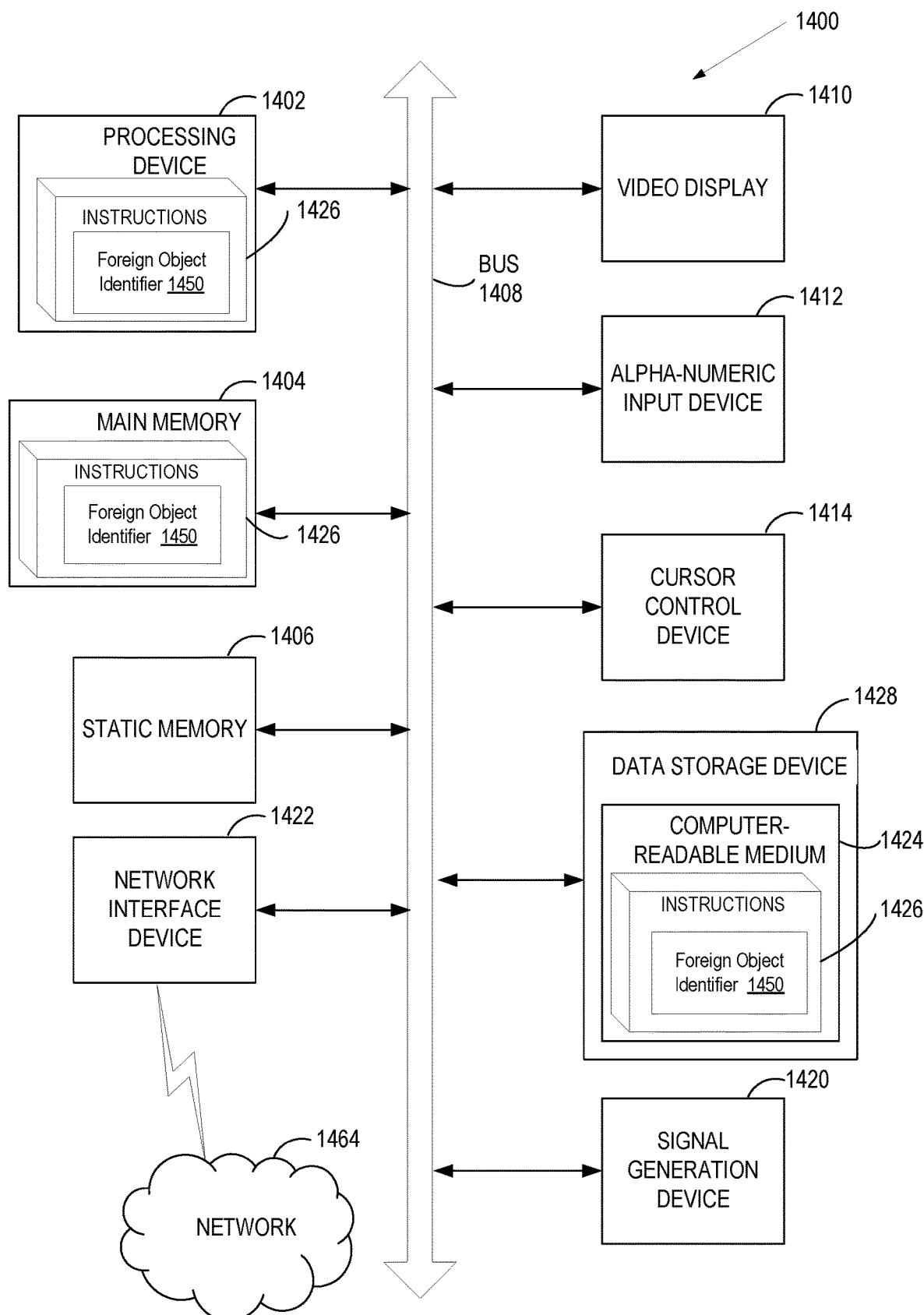
FIG. 14 illustrates a block diagram of an example computing device, in accordance with embodiments of the present disclosure.

FIG. 14 illustrates a diagrammatic representation of a machine in the example form of a computing device 1400 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein.

The example computing device 1400 includes a processing device 1402, a main memory 1404 (e.g., read-only memory (ROM), flash memory, dynamic random access memory (DRAM) such as synchronous DRAM (SDRAM), etc.), a static memory 1406 (e.g., flash memory, static random access memory (SRAM), etc.), and a secondary memory (e.g., a data storage device 1428), which communicate with each other via a bus 1408.

Processing device 1402 represents one or more general-purpose processors such as a microprocessor, central processing unit, or the like. More particularly, the processing device 1402 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1402 may also be one or more special-purpose processing devices such as an application specific integrated circuit (ASIC), a field programmable gate array (FPGA), a digital signal processor (DSP), network processor, or the like. Processing device 1402 is configured to execute the processing logic (instructions 1426) for performing operations and steps discussed herein.

The computing device 1400 may further include a network interface device 1422 for communicating with a network 1464. The computing device 1400 also may include a video display unit 1410 (e.g., a liquid crystal display (LCD) or a cathode ray tube (CRT)), an alphanumeric input device 1412 (e.g., a keyboard), a cursor control device 1414 (e.g., a mouse), and a signal generation device 1420 (e.g., a speaker).

The data storage device 1428 may include a machine-readable storage medium (or more specifically a non-transitory computer-readable storage medium) 1424 on which is stored one or more sets of instructions 1426 embodying any one or more of the methodologies or functions described herein. Wherein a non-transitory storage medium refers to a storage medium other than a carrier wave. The instructions 1426 may also reside, completely or at least partially, within the main memory 1404 and/or within the processing device 1402 during execution thereof by the computer device 1400, the main memory 1404 and the processing device 1402 also constituting computer-readable storage media.

The computer-readable storage medium 1424 may also be used to store a foreign object identifier 1450, which may correspond to similarly named foreign object identifier 115 of FIG. 1. The computer readable storage medium 1424 may also store a software library containing methods that call foreign object identifier 1450. While the computer-readable storage medium 1424 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing or encoding a set of instructions for execution by the machine and that cause the machine to perform any one or more of the methodologies of the present disclosure. The term "computer-readable storage medium" shall accordingly be taken to include, but not be limited to, solid-state memories, and optical and magnetic media.

FIG. 15 illustrates a method 1550 of orthodontic treatment using a plurality of appliances, in accordance with embodiments. The method 1550 can be practiced using a customized orthodontic appliance or appliance set generated based on a virtual 3D model of a patient's dental arch. The virtual 3D model may have been generated using intraoral images that were processed and optionally modified in accordance with embodiments described herein. In block 1560, a first orthodontic appliance is applied to a patient's teeth in order to reposition the teeth from a first tooth arrangement to a second tooth arrangement. In block 1570, a second orthodontic appliance is applied to the patient's teeth in order to reposition the teeth from the second tooth arrangement to a third tooth arrangement. The method 1550 can be repeated as necessary using any suitable number and combination of sequential appliances in order to incrementally reposition the patient's teeth from an initial arrangement to a target arrangement. The appliances can be generated all at the same stage or in sets or batches (e.g., at the beginning of a stage of the treatment), or the appliances can be fabricated one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

FIG. 16 illustrates a method 1600 for designing an orthodontic appliance. Some or all of the blocks of the method 1600 can be performed by any suitable data processing system or device, e.g., one or more processors configured with suitable instructions. In block 1610, a movement path to move one or more teeth from an initial arrangement to a target arrangement is determined. The initial arrangement can be determined from a mold or a scan of the patient's teeth or mouth tissue, e.g., using wax bites, direct contact scanning, x-ray imaging, tomographic imaging, sonographic imaging, and other techniques for obtaining information about the position and structure of the teeth, jaws, gums and other orthodontically relevant tissue. From the obtained data, a digital data set can be derived that represents the initial (e.g., pretreatment) arrangement of the patient's teeth and other tissues. Optionally, the initial digital data set is processed to segment the tissue constituents from each other. For example, data structures that digitally represent individual tooth crowns can be produced. Advantageously, digital models of entire teeth can be produced, including measured or extrapolated hidden surfaces and root structures, as well as surrounding bone and soft tissue.

The target arrangement of the teeth (e.g., a desired and intended end result of orthodontic treatment) can be received from a clinician in the form of a prescription, can be calculated from basic orthodontic principles, and/or can be extrapolated computationally from a clinical prescription. With a specification of the desired final positions of the teeth and a digital representation of the teeth themselves, the final position and surface geometry of each tooth can be specified to form a complete model of the tooth arrangement at the desired end of treatment.

Having both an initial position and a target position for each tooth, a movement path can be defined for the motion of each tooth. In some embodiments, the movement paths are configured to move the teeth in the quickest fashion with the least amount of round-tripping to bring the teeth from their initial positions to their desired target positions. The tooth paths can optionally be segmented, and the segments can be calculated so that each tooth's motion within a segment stays within threshold limits of linear and rotational translation. In this way, the end points of each path segment can constitute a clinically viable repositioning, and the aggregate of segment end points can constitute a clinically viable sequence of tooth positions, so that moving from one point to the next in the sequence does not result in a collision of teeth.

In block 1620, a force system to produce movement of the one or more teeth along the movement path is determined. A force system can include one or more forces and/or one or more torques. Different force systems can result in different types of tooth movement, such as tipping, translation, rotation, extrusion, intrusion, root movement, etc. Biomechanical principles, modeling techniques, force calculation/measurement techniques, and the like, including knowledge and approaches commonly used in orthodontia, may be used to determine the appropriate force system to be applied to the tooth to accomplish the tooth movement. In determining the force system to be applied, sources may be considered including literature, force systems determined by experimentation or virtual modeling, computer-based modeling, clinical experience, minimization of unwanted forces, etc.

The determination of the force system can include constraints on the allowable forces, such as allowable directions and magnitudes, as well as desired motions to be brought about by the applied forces. For example, in fabricating palatal expanders, different movement strategies may be desired for different patients. For example, the amount of force needed to separate the palate can depend on the age of the patient, as very young patients may not have a fully-formed suture. Thus, in juvenile patients and others without fully-closed palatal sutures, palatal expansion can be accomplished with lower force magnitudes. Slower palatal movement can also aid in growing bone to fill the expanding suture. For other patients, a more rapid expansion may be desired, which can be achieved by applying larger forces. These requirements can be incorporated as needed to choose the structure and materials of appliances; for example, by choosing palatal expanders capable of applying large forces for rupturing the palatal suture and/or causing rapid expansion of the palate. Subsequent appliance stages can be designed to apply different amounts of force, such as first applying a large force to break the suture, and then applying smaller forces to keep the suture separated or gradually expand the palate and/or arch.

The determination of the force system can also include modeling of the facial structure of the patient, such as the skeletal structure of the jaw and palate. Scan data of the palate and arch, such as X-ray data or 3D optical scanning data, for example, can be used to determine parameters of the skeletal and muscular system of the patient's mouth, so as to determine forces sufficient to provide a desired expansion of the palate and/or arch. In some embodiments, the thickness and/or density of the mid-palatal suture may be measured, or input by a treating professional. In other embodiments, the treating professional can select an appropriate treatment based on physiological characteristics of the patient. For example, the properties of the palate may also be estimated based on factors such as the patient's age—for example, young juvenile patients will typically require lower forces to expand the suture than older patients, as the suture has not yet fully formed.

In block 1630, an orthodontic appliance configured to produce the force system is determined. Determination of the orthodontic appliance, appliance geometry, material composition, and/or properties can be performed using a treatment or force application simulation environment. A simulation environment can include, e.g., computer modeling systems, biomechanical systems or apparatus, and the like.

In block 1640, instructions for fabrication of the orthodontic appliance or a mold that will be used to manufacture the orthodontic appliance are generated. The instructions can be configured to control a fabrication system or device in order to produce the orthodontic appliance and/or the mold. In some embodiments, the instructions are configured for manufacturing the orthodontic appliance using direct fabrication (e.g., stereolithography, selective laser sintering, fused deposition modeling, 3D printing, continuous direct fabrication, multi-material direct fabrication, etc.), in accordance with the various methods presented herein. In alternative embodiments, the instructions can be configured for indirect fabrication of the appliance, e.g., by direct 3D printing of the mold, and then thermoforming a plastic sheet over the mold.

Method 1600 may comprise additional blocks: 1) The upper arch and palate of the patient is scanned intraorally to generate three dimensional data of the palate and upper arch;

2) The three dimensional shape profile of the appliance is determined to provide a gap and teeth engagement structures as described herein.

Figure 17:
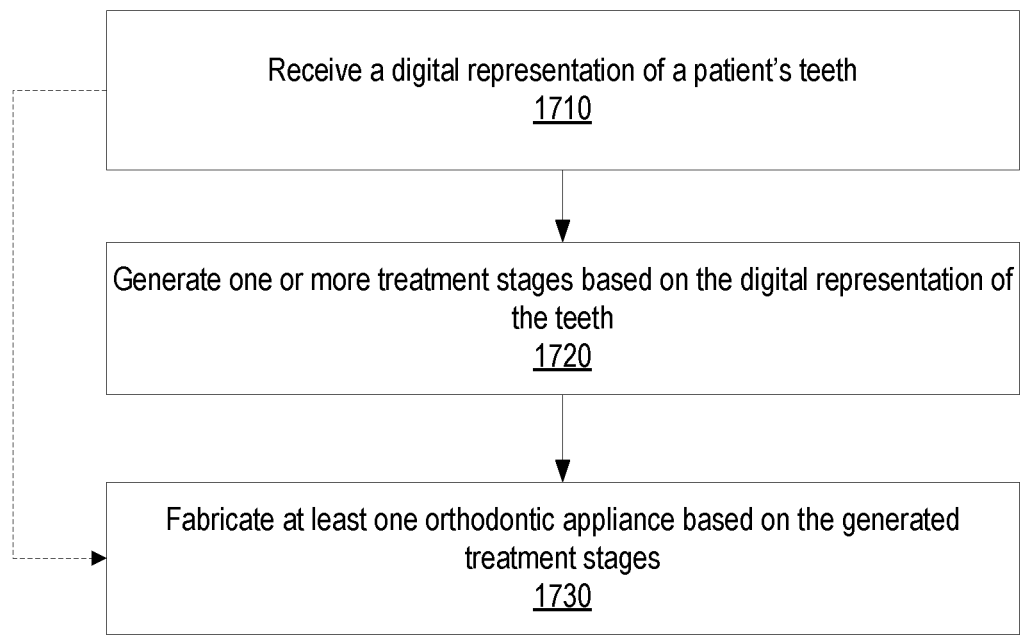
FIG. 17 illustrates a method for digitally planning an orthodontic treatment, in accordance with embodiments.

FIG. 17 illustrates a method 1700 for digitally planning an orthodontic treatment and/or design or fabrication of an appliance, in accordance with embodiments. The method 1700 can be applied to any of the treatment procedures described herein and can be performed by any suitable data processing system.

In block 1710, a digital representation of a patient's teeth is received. The digital representation can include surface topography data for the patient's intraoral cavity (including teeth, gingival tissues, etc.). The surface topography data can be generated by directly scanning the intraoral cavity, a physical model (positive or negative) of the intraoral cavity, or an impression of the intraoral cavity, using a suitable scanning device (e.g., a handheld scanner, desktop scanner, etc.).

In block 1720, one or more treatment stages are generated based on the digital representation of the teeth. The treatment stages can be incremental repositioning stages of an orthodontic treatment procedure designed to move one or more of the patient's teeth from an initial tooth arrangement to a target arrangement. For example, the treatment stages can be generated by determining the initial tooth arrangement indicated by the digital representation, determining a target tooth arrangement, and determining movement paths of one or more teeth in the initial arrangement necessary to achieve the target tooth arrangement. The movement path can be optimized based on minimizing the total distance moved, preventing collisions between teeth, avoiding tooth movements that are more difficult to achieve, or any other suitable criteria.

In block 1730, at least one orthodontic appliance is fabricated based on the generated treatment stages. For example, a set of appliances can be fabricated, each shaped according a tooth arrangement specified by one of the treatment stages, such that the appliances can be sequentially worn by the patient to incrementally reposition the teeth from the initial arrangement to the target arrangement. The appliance set may include one or more of the orthodontic appliances described herein. The fabrication of the appliance may involve creating a digital model of the appliance to be used as input to a computer-controlled fabrication system. The appliance can be formed using direct fabrication methods, indirect fabrication methods, or combinations thereof, as desired.

In some instances, staging of various arrangements or treatment stages may not be necessary for design and/or fabrication of an appliance. As illustrated by the dashed line in FIG. 17, design and/or fabrication of an orthodontic appliance, and perhaps a particular orthodontic treatment, may include use of a representation of the patient's teeth (e.g., receive a digital representation of the patient's teeth 1710), followed by design and/or fabrication of an orthodontic appliance based on a representation of the patient's teeth in the arrangement represented by the received representation.

It is to be understood that the above description is intended to be illustrative, and not restrictive. Many other embodiments will be apparent upon reading and understanding the above description. Although embodiments of the present disclosure have been described with reference to specific example embodiments, it will be recognized that the disclosure is not limited to the embodiments described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A method comprising:
receiving scan data comprising one or more two-dimensional (2D) intraoral images during an intraoral scan of a dental site;
identifying a representation of a foreign object in the one or more 2D intraoral images based on an analysis of the scan data;
modifying the one or more 2D intraoral images by removing the representation of the foreign object from the one or more 2D intraoral images;
converting the modified one or more 2D intraoral images in which the representation of the foreign object has been removed into three-dimensional (3D) data;
receiving additional scan data comprising a plurality of additional 2D intraoral images of the dental site during the intraoral scan;
converting the plurality of additional 2D intraoral images into additional 3D data; and
generating a virtual 3D model of the dental site using the 3D data and the additional 3D data.

2. The method of claim 1, further comprising:
identifying an additional representation of the foreign object in one of more additional 2D intraoral images of the plurality of additional 2D intraoral images of the dental site; and
modifying the one or more additional 2D intraoral images by removing the additional representation of the foreign object from the one or more additional 2D intraoral images;
wherein converting the plurality of additional 2D intraoral images into the additional 3D data comprises converting the modified one or more additional 2D intraoral images; and
wherein the foreign object is a stationary object that has a same position at the dental site in the one or more 2D intraoral images and the one or more additional 2D intraoral images.

3. The method of claim 1, further comprising:
analyzing the scan data to determine at least one of a reflectivity of the foreign object, a diffraction of the foreign object, a reactivity of the foreign object to a wavelength of light, a texture of the foreign object, a surface pattern of the foreign object, a color of the foreign object or a shape of the foreign object; and
identifying the representation of the foreign object based on at least one of the reflectivity of the foreign object, the diffraction of the foreign object, the reactivity of the foreign object to the wavelength of light, the texture of the foreign object, the surface pattern of the foreign object, the color of the foreign object or the shape of the foreign object.

4. The method of claim 1, further comprising:
performing image processing on the one or more 2D intraoral images to determine a plurality of shapes in the one or more 2D intraoral images, the plurality of shapes comprising a shape of the foreign object;
comparing the plurality of shapes in the one or more 2D intraoral images to a plurality of known shapes of reference objects; and determining that the shape of the foreign object matches a known shape of a reference object as a result of the comparing.

5. The method of claim 4, further comprising performing the following before the intraoral scan of the dental site:
entering a training mode;
receiving a plurality of images of the foreign object during the training mode;
generating a virtual model of the foreign object based on the plurality of images; and
adding at least one of the virtual model of the foreign object or the plurality of images of the foreign object to a reference object library that comprises the plurality of known shapes of the reference objects.

6. The method of claim 1, further comprising:
performing image processing of the one or more 2D intraoral images to identify at least one of a plurality of textures or a plurality of surface patterns in the one or more 2D intraoral images;
determining at least one of a texture of the plurality of textures or a surface pattern of the plurality of surface patterns that is not naturally occurring at the dental site; and
determining a contour of a region of the one or more 2D intraoral images having at least one of the texture or the surface pattern that is not naturally occurring at the dental site, wherein the region of the one or more 2D intraoral images within the contour is removed from the one or more 2D intraoral images.

7. The method of claim 6, wherein determining at least one of the texture or the surface pattern that is not naturally occurring at the dental site comprises at least one of:
a) comparing the plurality of textures identified in the one or more 2D intraoral images to a plurality of known textures of reference objects, and determining that the texture matches a known texture of a reference object as a result of the comparing;
b) comparing the plurality of surface patterns identified in the one or more 2D intraoral images to a plurality of known surface patterns of reference objects, and determining that the surface pattern matches a known surface pattern of a reference object as a result of the comparing;
c) comparing the plurality of textures identified in the one or more 2D intraoral images to a plurality of known textures that naturally occur at the dental site, and determining that the texture fails to match any known texture that naturally occurs in a mouth as a result of the comparing; or
d) comparing the plurality of surface patterns identified in the one or more 2D intraoral images to a plurality of known surface patterns that naturally occur at the dental site, and determining that the surface pattern fails to match any known surface pattern that naturally occurs in the mouth as a result of the comparing.

8. The method of claim 1, further comprising:
performing image processing of the one or more 2D intraoral images to identify a plurality of colors in the one or more 2D intraoral images;
determining at least one color of the plurality of colors that is not naturally occurring at the dental site; and
determining a contour of a region of the one or more 2D intraoral images having the at least one color that is not naturally occurring at the dental site, wherein the region of the one or more 2D intraoral images within the contour is removed from the one or more 2D intraoral images.

9. The method of claim 8, wherein:
determining the at least one color that is not naturally occurring at the dental site comprises performing the following for each pixel or voxel of the one or more 2D intraoral images:
determining, for each color channel of a color encoding system, at least one of a saturation value or an intensity value;
determining a tuple comprising at least one of the saturation value or the intensity value for each color channel of the color encoding system; and
determining that the tuple is outside of a specified color range; and
determining a contour of the region in the one or more 2D intraoral images having the at least one color that is not naturally occurring comprises determining a plurality of contiguous pixels or voxels having tuples that are outside of the specified color range.

10. The method of claim 1, further comprising:
receiving an indication that the foreign object is at the dental site, the indication comprising an identification of the foreign object;
querying a reference object library using the identification of the foreign object;
receiving a response to the query, the response comprising one or more known properties of the foreign object, the one or more known properties comprising at least one of a known reflectivity of the foreign object, a known diffraction of the foreign object, a known reactivity of the foreign object to a wavelength of light, a known texture of the foreign object, a known surface pattern of the foreign object, a known color of the foreign object or a known shape of the foreign object; and
using the one or more known properties of the foreign object to identify the representation of the foreign object in the one or more 2D intraoral images.

11. The method of claim 1, further comprising:
during the intraoral scan, generating a view of the dental site based on the modified one or more 2D intraoral images and the plurality of additional 2D intraoral images;
generating an outline of the foreign object;
adding the outline of the foreign object to the view; and
providing a user interface that enables a user to select the outline of the foreign object, wherein user selection of the outline of the foreign object causes the representation of the foreign object to be added back to the one or more 2D intraoral images and further causes the foreign object to be added to a reference object library of known objects not to be filtered out.

12. The method of claim 1, further comprising performing the following prior to modifying the one or more 2D intraoral images:
determining a confidence value associated with the representation of the foreign object;
determining that the confidence value is below a confidence threshold;
presenting an option to a) remove the representation of the foreign object from the one or more 2D intraoral images or b) leave the representation of the foreign object in the one or more 2D intraoral images; and
receiving a user selection to remove the representation of the foreign object from the one or more 2D intraoral images.

13. The method of claim 12, further comprising:
determining one or more properties of the foreign object, the one or more properties comprising at least one of a reflectivity of the foreign object, a diffraction of the foreign object, a reactivity of the foreign object to a wavelength of light, a texture of the foreign object, a surface pattern of the foreign object, a color of the foreign object or a shape of the foreign object; and adding an entry for the foreign object to a reference object library of known foreign objects to be filtered out.

14. The method of claim 12, wherein identifying the representation of the foreign object comprises:

processing the one or more 2D intraoral images using a machine learning model that has been trained to identify foreign objects at dental sites; and receiving an output of the machine learning model, wherein the output comprises a binary mask that has a number of entries that is equal to a number of pixels or voxels in the one or more 2D intraoral images, wherein entries associated with pixels or voxels that are part of the foreign object have a first value and wherein entries associated with pixels or voxels that are not part of the foreign object have a second value;

wherein the one or more 2D intraoral images are modified using the binary mask.

15. A non-transitory computer readable medium comprising instructions that, when executed by a processing device, cause the processing device to perform operations comprising:

receiving scan data comprising one or more two-dimensional (2D) intraoral images during an intraoral scan of a dental site;

identifying a representation of a foreign object in the one or more 2D intraoral images based on an analysis of the scan data;

modifying the one or more 2D intraoral images by removing the representation of the foreign object from the one or more 2D intraoral images;

converting the modified one or more 2D intraoral images in which the representation of the foreign object has been removed into three-dimensional (3D) data;

receiving additional scan data comprising a plurality of additional 2D intraoral images of the dental site during the intraoral scan;

converting the plurality of additional 2D intraoral images into additional 3D data; and generating a virtual 3D model of the dental site using the 3D data and the additional 3D data.

16. The non-transitory computer readable medium of claim 15, the operations further comprising:

identifying an additional representation of the foreign object in one of more additional 2D intraoral images of the plurality of additional 2D intraoral images of the dental site; and modifying the one or more additional 2D intraoral images by removing the additional representation of the foreign object from the one or more additional 2D intraoral images;

wherein converting the plurality of additional 2D intraoral images into the additional 3D data comprises converting the modified one or more additional 2D intraoral images; and wherein the foreign object is a stationary object that has a same position at the dental site in the one or more 2D intraoral images and the one or more additional intraoral images.

17. The non-transitory computer readable medium of claim 15, the operations further comprising:

analyzing the scan data to determine at least one of a reflectivity of the foreign object, a diffraction of the foreign object, a reactivity of the foreign object to a wavelength of light, a texture of the foreign object, a surface pattern of the foreign object, a color of the foreign object or a shape of the foreign object; and identifying the representation of the foreign object based on at least one of the reflectivity of the foreign object, the diffraction of the foreign object, the reactivity of the foreign object to a wavelength of light, the texture of the foreign object, the surface pattern of the foreign object, the color of the foreign object or the shape of the foreign object.

18. The non-transitory computer readable medium of claim 15, the operations further comprising:

performing image processing on the one or more 2D intraoral images to determine a plurality of shapes in the one or more 2D intraoral images, the plurality of shapes comprising a shape of the foreign object;

comparing the plurality of shapes in the one or more 2D intraoral images to a plurality of known shapes of reference objects; and determining that the shape of the foreign object matches a known shape of a reference object as a result of the comparing.

19. The non-transitory computer readable medium of claim 18, the operations further comprising:

entering a training mode;

receiving a plurality of images of the foreign object during the training mode;

generating a virtual model of the foreign object based on the plurality of images; and adding at least one of the virtual model of the foreign object or the plurality of images of the foreign object to a reference object library that comprises the plurality of known shapes of the reference objects.

20. The non-transitory computer readable medium of claim 15, the operations further comprising:

performing image processing of the one or more 2D intraoral images to identify at least one of a plurality of textures or a plurality of surface patterns in the one or more 2D intraoral images;

determining at least one of a texture of the plurality of textures or a surface pattern of the plurality of surface patterns that is not naturally occurring at the dental site; and determining a contour of a region of the one or more 2D intraoral images having at least one of the texture or the surface pattern that is not naturally occurring at the dental site, wherein the region of the one or more 2D intraoral images within the contour is removed from the one or more 2D intraoral images.

21. The non-transitory computer readable medium of claim 20, wherein determining at least one of the texture or the surface pattern that is not naturally occurring at the dental site comprises at least one of:

a) comparing the plurality of textures identified in the one or more 2D intraoral images to a plurality of known textures of reference objects, and determining that the texture matches a known texture of a reference object as a result of the comparing;

b) comparing the plurality of surface patterns identified in the one or more 2D intraoral images to a plurality of known surface patterns of reference objects, and determining that the surface pattern matches a known surface pattern of a reference object as a result of the comparing;

c) comparing the plurality of textures identified in the one or more 2D intraoral images to a plurality of known textures that naturally occur at the dental site, and determining that the texture fails to match any known texture that naturally occurs in a mouth as a result of the comparing; or d) comparing the plurality of surface patterns identified in the one or more 2D intraoral images to a plurality of known surface patterns that naturally occur at the dental site, and determining that the surface pattern fails to match any known surface pattern that naturally occurs in the mouth as a result of the comparing.

22. The non-transitory computer readable medium of claim 15, the operations further comprising:

performing image processing of the one or more 2D intraoral images to identify a plurality of colors in the one or more 2D intraoral images;

determining at least one color of the plurality of colors that is not naturally occurring at the dental site; and determining a contour of a region of the one or more 2D intraoral images having the at least one color that is not naturally occurring at the dental site, wherein the region of the one or more 2D intraoral images within the contour is removed from the one or more 2D intraoral images.

23. A system comprising:

a handheld scanner to perform an intraoral scan; and a non-transitory computer readable medium comprising instructions that, when executed by a processor, cause the processor to perform operations comprising:

receiving one or more two-dimensional (2D) intraoral images during an intraoral scan of a dental site;

identifying a representation of a foreign object in the one or more 2D intraoral images based on at least one of a reflectivity of the foreign object, a diffraction of the foreign object, a reactivity of the foreign object to a wavelength of light, a texture of the foreign object, a surface pattern of the foreign object, a color of the foreign object or a shape of the foreign object;

modifying the one or more 2D intraoral images by removing the representation of the foreign object from the one or more 2D intraoral images;

converting the modified one or more 2D intraoral images in which the representation of the foreign object has been removed into three-dimensional (3D) data;

receiving a plurality of additional 2D intraoral images of the dental site during the intraoral scan;

converting the plurality of additional 2D intraoral images into additional 3D data; and generating a virtual 3D model of the dental site using the 3D data and the additional 3D data.

\* \* \* \* \*